US012605325B2

(12) United States Patent
Naiberk et al.

(10) Patent No.: US 12,605,325 B2
(45) Date of Patent: Apr. 21, 2026

(54) HAIR STYLING COMPOSITIONS FOR IMPROVING THE ELONGATION OF HAIR CURLS

(71) Applicant: L'OREAL, Paris (FR)

(72) Inventors: Emma Naiberk, Maplewood, NJ (US); Seyma Aslan, Clifton, NJ (US); Rita Chokshi, Monroe Township, NJ (US); Xian Zhi Zhou, Millburn, NJ (US)

(73) Assignee: L'OREAL, Paris (FR)

( * ) Notice: Subject to any disclaimer, the term of this patent is extended or adjusted under 35 U.S.C. 154(b) by 1237 days.

(21) Appl. No.: 16/916,265

(22) Filed: Jun. 30, 2020

(65) Prior Publication Data

US 2021/0401719 A1 Dec. 30, 2021

(51) Int. Cl.

| | |
|---|---|
| ***A61K 8/73*** | (2006.01) |
| ***A61K 8/34*** | (2006.01) |
| ***A61K 8/39*** | (2006.01) |
| ***A61K 8/41*** | (2006.01) |
| ***A61K 8/92*** | (2006.01) |
| ***A61Q 5/06*** | (2006.01) |

(52) U.S. Cl.

CPC .............. *A61K 8/732* (2013.01); *A61K 8/345* (2013.01); *A61K 8/416* (2013.01); *A61K 8/922* (2013.01); *A61Q 5/06* (2013.01)

(58) Field of Classification Search

CPC ........ A61K 8/732; A61K 8/345; A61K 8/416; A61K 8/922; A61K 8/39; A61K 8/375; A61Q 5/06

See application file for complete search history.

(56) References Cited

U.S. PATENT DOCUMENTS

| | | | | |
|---|---|---|---|---|
| 9,918,922 | B1 * | 3/2018 | Botto | A61K 8/60 |
| 2018/0311140 | A1 * | 11/2018 | Perner | A61K 8/92 |
| 2019/0091493 | A1 * | 3/2019 | Suleiman | A61K 8/8152 |

FOREIGN PATENT DOCUMENTS

| | | | |
|---|---|---|---|
| EP | 0829255 | A2 | 3/1998 |
| EP | 0829255 | A3 | 3/1998 |

OTHER PUBLICATIONS

Bis-Diglyceryl Polyacyladipate-2, https://www.surfactant.top/en/saa/?type=detail&id=2370, 3 pages. Oct. 20, 2014 (Year: 2014 (Year: 2014).*

(Continued)

*Primary Examiner* — Trevor Love
*Assistant Examiner* — Janet Joseph
(74) *Attorney, Agent, or Firm* — POLSINELLI PC

(57) ABSTRACT

Provided are hair styling compositions including about 5 wt. % or more of hydrogenated starch hydrolysate; about 3 wt. % or more of polyol, having a weight ratio of the total amount of hydrogenated starch hydrolysate to the total amount of polyol of from 1:1 to 10:1; about 1 to about 10 wt. % of a plant or vegetable based oil, wherein the plant or vegetable based oil comprises shea butter, castor oil, or a combination thereof; about 0.1 to about 7 wt. % of a cationic surfactant; about 0.5 to about 10 wt. % of emulsifiers chosen from a glyceryl ester, a fatty alcohol, and a combination thereof; and water, wherein all weight percentages are based on the total weight of the hair styling composition. Methods for styling hair using the hair styling compositions are also provided herein.

26 Claims, 5 Drawing Sheets

(56) References Cited

OTHER PUBLICATIONS

International Search Report and Written Opinion issued Nov. 17, 2021 for corresponding PCT Application No. PCT/US2021/039541.
Preliminary Search Report and Written Opinion issued on May 6, 2021 for corresponding French Application No. 2008566.
Database GNPD [Online]; MINTEL; "The Scalp Treatment Pack," 2019 XP055801906.
Database GNPD [Online]; MINTEL; "Moisturising & Smoothing Hair Mask," 2020 XP055801910.

* cited by examiner

| Style | Dry Twist | Open Twist |
|---|---|---|
| Images |   |     |

HAIR STYLING COMPOSITIONS FOR IMPROVING THE ELONGATION OF HAIR CURLS

FIELD OF THE DISCLOSURE

The present disclosure relates to hair styling compositions for improving the moisture content and visual appearance of hair curls, and particularly to hair compositions that improve curl definition, curl hold, hair moisture, frizz control while providing an elongation benefit to the curls.

BACKGROUND OF THE DISCLOSURE

Many consumers desire to use cosmetic and care compositions that enhance the appearance of hair, e.g., by changing the color, style, and/or shape of the hair, and/or by imparting various cosmetic properties to hair, such as shine and conditioning. There are many techniques and compositions for styling or altering the shape of hair. For example, hair care products referred to as "hair relaxers" or "hair straighteners" can relax or straighten curly or kinky hair, including wavy hair. Straightening or relaxing the curls of very curly hair may increase the manageability and ease of styling of such hair. Compositions for permanent waving the hair will impart a curl or a wave to otherwise straight hair. Different types of compositions can be applied onto hair in order to change its shape and make it more manageable, such as alkaline and acidic compositions.

While relaxing, straightening, perming, and waving compositions can effectively alter the shape of the hair, these chemical treatments can damage the hair fibers and/or irritate the scalp. Thus, in order to reduce or avoid damage to hair, as well as to improve the cosmetic performance of the compositions, different types of hair styling products have been developed by manufacturers that are aimed to help consumers achieve a desired look, including one or more of fuller hair, thicker hair, sleek and straight hair, frizz-free hair, and defined curls. These products are typically provided in forms that are applied after the shampooing and conditioning processes are completed.

In one example, styling products are available that provide protection against external factors such as protection from moisture to minimize or reduce frizziness. To achieve this benefit, a water-resistant film or coating may be applied to the hair using film-forming polymers. Product formulations that include these polymers can tend to be viscous, e.g. as the concentration of the polymer increases its viscosity builds up rapidly. Translated to styling applications, as the solvent evaporates, the polymer solution becomes thicker on the hair surface, leaving a sticky or tacky film residue on the hair. This often leaves hair with films that are hard and brittle and, therefore, have a crunchy feel or sound when manipulated.

Thus, as an object of this disclosure, provided are hair styling compositions that provided improved hair properties.

SUMMARY OF THE DISCLOSURE

The present disclosure relates to hair styling compositions for improving the moisture content and visual appearance of hair curls, and particularly to hair compositions that improve curl definition, curl hold, hair moisture, frizz control while simultaneously providing an elongation benefit to the curls. The hair styling compositions of the instant disclosure may provide a natural look and feel, impart good styling benefits to hair and lack the drawbacks of current products, such as the stiff and crunchy effects created by the thick coatings of many styling products. The hair styling compositions may also provide multiple benefits, e.g., combining frizz reduction and long lasting style hold/control with softening, curl definition, and curl elongation.

The inventors discovered that hair styling compositions of the instant disclosure may also provide elongation to hair curls (e.g., by stretching the curls while maintain curl definition), which may desirably increase the length of the hair. Additionally, in certain instances, the hair styling compositions provide elongation to hair curls without utilizing significant amounts of oils and/or waxes that make the hair feel heavy and, often, look greasy or dirty.

The hair styling compositions according to an aspect of the disclosure typically includes:

(a) about 5 wt. % or more of hydrogenated starch hydrolysate;

(b) about 3 wt. % or more of polyol,
  wherein a weight ratio of the total amount of hydrogenated starch hydrolysate to the total amount of polyol is from 1:1 to 10:1;

(c) about 1 to about 10 wt. % of a plant or vegetable based oil, wherein the plant or vegetable based oil comprise shea butter, castor oil, or a combination thereof;

(d) about 0.1 to about 7 wt. % of a cationic surfactant;

(e) about 0.5 to about 10 wt. % of emulsifiers, wherein the emulsifiers are chosen from:
  a glyceryl ester,
  a fatty alcohol, and
  a mixture thereof; and (f) water,
  wherein all weight percentages are based on the total weight of the hair styling composition.

The hair styling compositions may be formulated to have a weight ratio of the total amount of hydrogenated starch hydrolysate to the total amount of polyol is 1:1 to 5:1. In some cases, the weight ratio of the total amount of hydrogenated starch hydrolysate to the total amount of polyol is 1:1 to 2:1. In some cases, the storage modulus of the hair styling composition increases with an amount drying time. In further cases, the yield stress of the hair styling composition increases with an amount of drying time.

The hair styling compositions may include about 3 wt. % to about 15 wt. % of polyol. The polyol may be chosen from ethylene glycol, propylene glycol, butylene glycol, hexylene glycol, pentylene glycol, diethylene glycol, dipropylene glycol, 1,3 propanediol, glycerin, diglycerin, polyethylene glycols, and a mixture thereof. In at least one instance, the polyol is glycerin.

The plant or vegetable based oil may include both castor oil and shea butter. In some cases, the plant or vegetable based oil further includes coconut oil, soybean oil, canola oil, rapeseed oil, corn oil, cottonseed oil, olive oil, palm oil, peanut oil, safflower oil, sesame oil, sunflower oil, linseed oil, palm kernel oil, tung oil, jatropha oil, mustard oil, camelina oil, pennycress oil, castor oil, wheatgerm oil, apricot kernel oil, pistachio oil, poppy oil, pine oil, avocado oil, hazel nut oil, grapeseed oil, colza oil, cade oil, peach kernel oil, coffee bean oil, jojoba oil, or a mixture thereof.

The hair styling composition may include a cationic surfactant that is chosen from cetrimonium chloride, steartrimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, and a mixture thereof. In some cases, the cationic surfactant is behentrimonium chloride.

Non-limiting examples of fatty alcohols that may incorporated into the hair styling composition include cetyl alcohol, stearyl alcohol, cetearyl alcohol (combination of cetyl alcohol and stearyl alcohol), behenyl alcohol, lauryl alcohol (1-dodecanol); myristic or myristyl alcohol (1-tetradecanol), arachidyl alcohol (1-eicosanol), lignoceryl alcohol (1-tetracosanol); ceryl alcohol (1-hexacosanol); montanyl alcohol (1-octacosanol); myricylic alcohol (1-triacontanol), decyl alcohol, undecyl alcohol, or a mixture thereof. In at least one instance, the fatty alcohol is cetearyl alcohol.

The emulsifiers of the hair styling composition may further comprise about 0.1 to about 9.8 wt. % of a fatty ester that is not glyceryl ester. For instance, the hair styling composition may include a fatty ester other than glyceryl ester that is chosen from isopropyl esters, cetyl esters, isopropyl myristate, isopropyl laurate, isopropyl oleate, isopropyl palmitate, isopropyl stearate, and a mixture thereof.

Additionally or alternatively, the hair styling composition may include about 0.1 to about 10 wt. % of a thickening agent. In some cases, the thickening agent is chosen from hydroxypropyl guar, xanthan gum, guar gum, biosaccharide gum, cellulose, acacia seneca gum, sclerotium gum, agarose, pechtin, gellan gum, ammonium polyacryloyldimethyl taurate, ammonium acryloyldimethyltaurate/VP copolymer, sodium polyacrylate, acrylates copolymers, polyacrylamide, carbomer, acrylates/C10-30 alkyl acrylate crosspolymer, acrylates/beheneth-25 methacrylate copolymer, and a mixture thereof.

According to another aspect of the disclosure, a method for hair styling typically includes:

- (I) applying a hair styling composition to hair, the hair styling composition comprising:
  - (a) about 5 wt. % or more of hydrogenated starch hydrolysate;
  - (b) about 3 wt. % or more of polyol,
    - wherein a weight ratio of the total amount of hydrogenated starch hydrolysate to the total amount of polyol is from 1:1 to 10:1;
  - (c) about 1 to about 10 wt. % of a plant or vegetable based oil, wherein the plant or vegetable based oil comprise shea butter, castor oil, or a combination thereof;
  - (d) about 0.1 to about 7 wt. % of a cationic surfactant;
  - (e) about 0.5 to about 10 wt. % of emulsifiers, wherein the emulsifiers are chosen from:
    - a glyceryl ester,
    - a fatty alcohol, and
    - a mixture thereof; and
  - (f) water, wherein all weight percentages are based on the total weight of the hair styling composition;
- (II) styling the hair.

The method for hair styling may include styling the hair within 20 minutes of application of the hair styling composition to the hair.

BRIEF DESCRIPTION OF THE DRAWINGS

Implementation of the present technology will now be described, by way of example only, with reference to the attached figures, wherein.

Figure 1:
FIG. 1 provides an image using a bright field equipped microscope of the microstructure of the emulsion of an exemplary hair styling composition in accordance with aspects of the disclosure.

It should be understood that the various aspects are not limited to the arrangements and instrumentality shown in the drawings.

DETAILED DESCRIPTION OF THE DISCLOSURE

The present disclosure relates to hair styling compositions for improving the moisture content and visual appearance of hair curls, and particularly to hair compositions that improve curl definition, curl hold, hair moisture, frizz control while simultaneously providing an elongation benefit to the curls. The hair styling compositions of the instant disclosure may provide a natural look and feel, impart good styling benefits to hair and lack the drawbacks of current products, such as the stiff and crunchy effects created by the thick coatings of many styling products. The hair styling compositions may also provide a long last style control and multiple cosmetic benefits, e.g., combining frizz reduction, softening, curl definition, and curl elongation.

Figure 2:
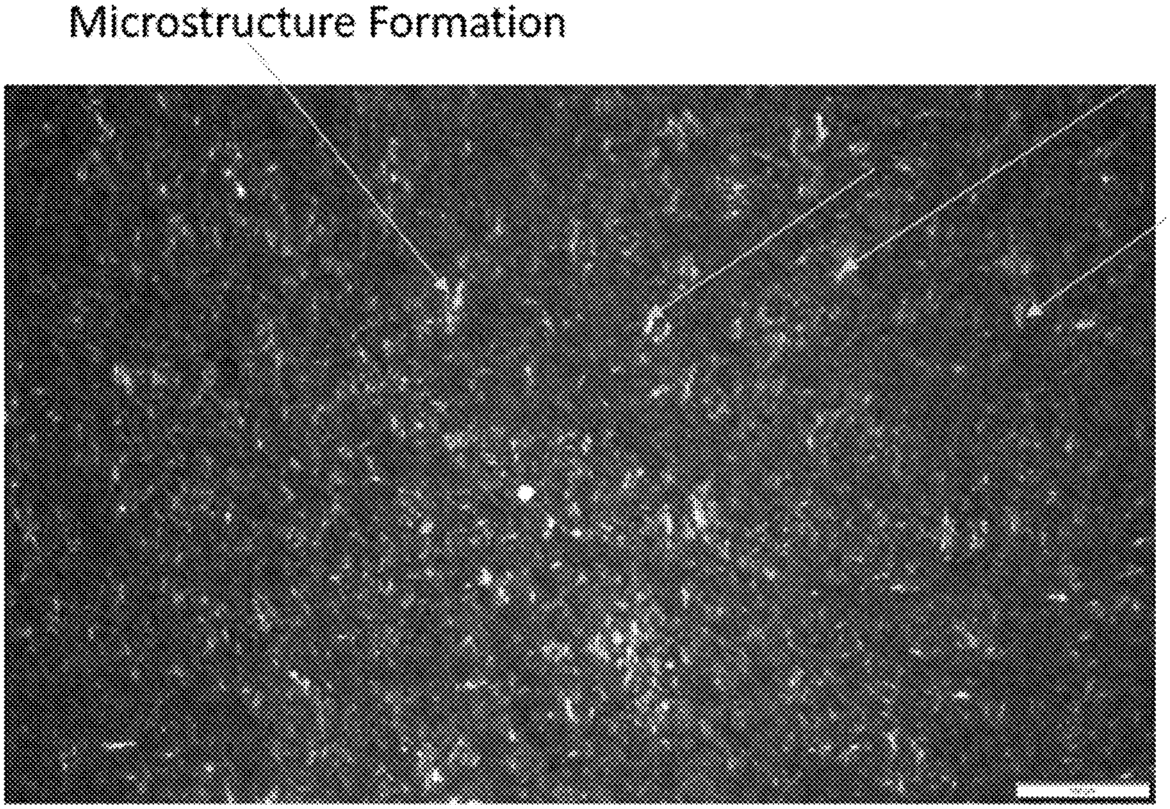
FIG. 2 provides an image using a polarized light equipped microscope of the microstructure of the exemplary hair styling composition of FIG. 1.

The inventors discovered that hair styling compositions of the instant disclosure may also provide elongation to hair curls (e.g., by stretching the curls while maintaining curl definition), which may desirably increase the length of the hair. Without being limited to any specific theory, it is believed that certain combinations of ingredients (such as the combination of cationic surfactant and fatty alcohol & glyceryl stearate) in specific ratios provides hair styling compositions that have an oil-in-water emulsion with a microstructure that holds water therein, such that the hair stays moisturized. For instance, it is believed that in some cases the hair styling compositions form lamellar gel network to trap the water. The lamellar gel network and the rheological properties of the coatings formed therefrom may provide enhanced durability in addition to the improved hair moisture and cosmetic effects. Images of the microstructure of the oil-in-water emulsion of an exemplary hair styling composition under a microscope using bright field and polarized light equipment are provided in FIGS. 1 and 2. As seen in FIGS. 1 and 2, the microstructure of the exemplary hair styling composition retained significant amounts of water.

In addition, the inventors discovered surprising benefits from utilizing a combination of a cationic quaternary ammonium compound (preferably behentrimonum chloride), a polyol (preferably glycerin), and a hydrogenated starch hydrolysate. Without being limited to any specific theory, it is believed that that the unique foregoing combination provides an unexpected increase in hydrogen bonding with hair.

The hair styling compositions according to an aspect of the disclosure typically includes:

(a) about 5 wt. % or more of hydrogenated starch hydrolysate;

(b) about 3 wt. % or more of polyol, wherein a weight ratio of the total amount of hydrogenated starch hydrolysate to the total amount of polyol is from 1:1 to 10:1;

(c) about 1 to about 10 wt. % of a plant or vegetable based oil, wherein the plant or vegetable based oil comprise shea butter, castor oil, or a combination thereof;

(d) about 0.1 to about 7 wt. % of a cationic surfactant;

(e) about 0.5 to about 10 wt. % of emulsifiers, wherein the emulsifiers are chosen from:
a glyceryl ester,
a fatty alcohol, and
a mixture thereof; and (f) water,
wherein all weight percentages are based on the total weight of the hair styling composition.

In some cases, the weight ratio of the total amount of hydrogenated starch hydrolysate to the total amount of polyol is from 1:1 to 10:1, 1:1 to 9:1, 1:1 to 8:1, 1:1 to 7:1, 1:1 to 6:1, 1:1 to 5:1, 1:1 to 4:1, 1:1 to 3:1, or 1:1 to 2:1. Additionally or alternatively, in certain instances, the hair styling compositions provide elongation to hair curls without utilizing significant amounts of oils and/or waxes that make the hair feel heavy and, often, look greasy or dirty. For example, the hair styling composition may be formulated to have about 30 wt. % or less, about 20 wt. % or less, about 15 wt. % or less, about 10 wt. % or less, about 5 wt. % or less of oils and/or waxes.

According to another aspect of the disclosure, a method for hair styling typically includes:

(I) applying a hair styling composition to hair, the hair styling composition comprising:

(a) about 5 wt. % or more of hydrogenated starch hydrolysate;

(b) about 3 wt. % or more of polyol,
wherein a weight ratio of the total amount of hydrogenated starch hydrolysate to the total amount of polyol is from 1:1 to 10:1;

(c) about 1 to about 10 wt. % of a plant or vegetable based oil, wherein the plant or vegetable based oil comprise shea butter, castor oil, or a combination thereof;

(d) about 0.1 to about 7 wt. % of a cationic surfactant;

(e) about 0.5 to about 10 wt. % of emulsifiers, wherein the emulsifiers are chosen from:
a glyceryl ester,
a fatty alcohol, and
a mixture thereof; and (f) water, wherein all weight percentages are based on the total weight of the hair styling composition;

(II) styling the hair.

The method for hair styling may include styling the hair within 20 minutes of application of the hair styling composition to the hair. For example, the hair may be styled within 20 minutes, within about 18 minutes, within about 16 minutes, within about 14 minutes, within about 12 minutes, within about 10 minutes, within about 8 minutes, within about 6 minutes, within about 5 minutes, within about 4 minutes, within about 3 minutes, within about 2 minutes or within about 1 minute of application of the hair styling composition to the hair.

In at least one instance, the hair styling composition is applied while the hair is wet and/or damp. The methods for hair styling may also include styling the hair using a "wash and go" or "twist out" method. As used herein, "wash and go" refers to the application of the hair styling composition, section by section, to wet or damp hair and letting it air dry. "Twist out" refers to the application of the hair styling composition on wet hair and twisting small sections of the hair and letting it air dry. The twist out steps are typically used to manipulate the curl pattern in order to provide elongation while maintaining other styling benefits.

The method of the present invention comprises applying the hair styling composition of the present disclosure onto hair, wherein the method imparts to hair one or more of:
shaping or styling benefits;
curl elongation (or curl stretching or curl lengthening);
curl definition;
curl retention;
long-lasting curl definition;
humidity-resistant curl definition;
frizz control;
styling/shaping hold;
smoothness;
softness;
natural feel;
hydration;
light-weight feel;
shine; and/or
crunch.

The above hair styling compositions and methods of use thereof feature a unique combinations of ingredients that advantageously provide frizz control, curl definition, curl retention, discipline, hold/control, styling/shaping, long lasting or humidity-resistant styling and curl care benefits together with natural feel, light-weight feel, softness, and smoothness. The hair styling compositions described herein may be in any suitable physical form. Suitable forms include, but are not limited to low to moderate viscosity liquids, lotions, milks, gel creams, creams, pastes, clays, conditioners, masks, and the like.

In some cases, the storage modulus of the hair styling composition increases with an amount drying time. In further cases, the yield stress of the hair styling composition increases with an amount of drying time. The amount of time may be from 1 minute, 2 minutes, 5 minutes, 10 minutes, 15 minutes, 20 minutes, 25 minutes, 30 minutes, 45 minutes, 1 hour and/or up to 1 hour, 2 hours, 3 hours, 4 hours, 5 hours, 6 hours, 7 hours, 8 hours, 9 hours, and/or 10 hours, including all ranges and subranges therebetween.

The hair styling compositions may be packaged in a variety of different containers, such as, for example, a ready-to-use container. Non-limiting examples of useful packaging include tubes, jars, caps, unit dose packages, and bottles, including squeezable tubes and bottles and spray bottles.

Suitable components, such as those listed below, may be included or excluded from the formulations for the hair styling compositions depending on the specific combination of other components, the form of the hair styling compositions, and/or the use of such hair styling compositions.

Hydrogenated Starch Hydrolysate

The hair styling composition includes hydrogenated starch hydrolysate, typically in an amount of about 5 wt. % or more, based on the total weight of the hair styling composition. In some cases, the amount of hydrogenated starch hydrolysate in the hair styling composition is about 5 wt. % or more, about 6 wt. % or more about 7 wt. % or more, about 8 wt. % or more, about 9 wt. % or more, about 10 wt.

% or more, about 11 wt. % or more, about 12 wt. % or more, about 13 wt. % or more, about 14 wt. % or more, about 15 wt. % or more, about 16 wt. % or more, about 17 wt. % or more, about 18 wt. % or more, about 19 wt. % or more, about 20 wt. % or more, based on the total weight of the hair styling composition.

Additionally or alternatively, the hair styling compositions may include hydrogenated starch hydrolysate in an amount of about 5 to about 20 wt. %, based on the total weight of the hair styling composition. For example, the hydrogenated starch hydrolysate may be present in the hair styling composition in an amount of about 6 to about 20 wt. %, about 7 to about 20 wt. %, about 8 to about 20 wt. %, about 10 to about 20 wt. %, about 12 to about 20 wt. %, about 15 to about 20 wt. %, about 18 to about 20 wt. %; about 5 to about 18 wt. %, about 6 to about 18 wt. %, about 7 to about 18 wt. %, about 8 to about 18 wt. %, about 10 to about 18 wt. %, about 12 to about 18 wt. %, about 15 to about 18 wt. %; about 5 to about 16 wt. %, about 6 to about 16 wt. %, about 7 to about 16 wt. %, about 8 to about 16 wt. %, about 10 to about 16 wt. %, about 12 to about 16 wt. %; about 5 to about 14 wt. %, about 6 to about 14 wt. %, about 7 to about 14 wt. %, about 8 to about 14 wt. %, about 10 to about 14 wt. %, about 12 to about 14 wt. %, including ranges and subranges therebetween, based on the total weight of the hair styling composition.

The hydrogenated starch hydrolysate are typically mixtures of sugar alcohols, including sorbitol, maltitol, maltotriitol and other hydrogenated oligosaccharides and polysaccharides. In some instances, the hydrogenated starch hydrolysate may consist of one or more of sorbitol, maltitol, maltotriitol and other hydrogenated oligosaccharides and polysaccharides.

Polyol(s)

The hair styling compositions include one or more polyols, e.g., such as those chosen from ethylene glycol, propylene glycol, butylene glycol, hexylene glycol, pentylene glycol, diethylene glycol, dipropylene glycol, 1,3 propanediol, glycerin, diglycerin, polyethylene glycols and a mixture thereof. The amount of polyol(s) present in the hair styling composition is typically about 3 wt. % or more, based on the total weight of the hair styling composition. For example, the amount of polyol(s) in the hair styling composition may be about 4 wt. % or more, about 5 wt. % or more, about 6 wt. % or more, about 7 wt. % or more, about 8 wt. % or more, about 9 wt. % or more, about 10 wt. % or more, about 11 wt. % or more, about 12 wt. % or more, about 13 wt. % or more, about 14 wt. % or more, about 15 wt. % or more, about 16 wt. % or more, about 17 wt. % or more, about 18 wt. % or more, about 19 wt. % or more, about 20 wt. % or more, based on the total weight of the hair styling composition.

Additionally or alternatively, the one or more polyol is present in the hair styling composition in an amount of about 3 to about 20 wt. %, based on the total weight of the hair styling composition. For example, the one or more polyol may be present in the hair styling composition in an amount of about 3 to about 20 wt. %, about 5 to about 20 wt. %, about 7 to about 20 wt. %, about 9 to about 20 wt. %, about 12 to about 20 wt. %, about 15 to about 20 wt. %, about 18 to about 20 wt. %; about 3 to about 15 wt. %, about 5 to about 15 wt. %, about 7 to about 15 wt. %, about 9 to about 15 wt. %, about 12 to about 15 wt. %; about 3 to about 10 wt. %, about 5 to about 10 wt. %, about 7 to about 10 wt. %; about 3 to about 8 wt. %, about 5 to about 8 wt. %; about 3 to about 6 wt. %, or about 5 to about 6 wt. %, including ranges and subranges therebetween, based on the total weight of the hair styling composition.

The term "polyol" should be understood as meaning, within the meaning of the present disclosure, an organic molecule comprising at least two free hydroxyl groups. The polyols of the hair styling composition may be glycols or compounds with numerous hydroxyl groups. In some cases, the one or more polyols is/are selected from the group consisting of $C_2$-$C_{32}$ polyols. The one or more polyols may be liquid at ambient temperature (25° C.). The one or more polyols may have from 2 to 32 carbon atoms, from 3 to 16 carbon atoms, or from 3 to 12 carbon atoms.

Polyols that may be included in the hair styling composition, in certain instances, include ethylene glycol, propylene glycol, butylene glycol, hexylene glycol, pentylene glycol, 1,3-propanediol, dipropylene glycol, caprylyl glycol, glycerin, diglycerin, diethylene glycol, and dipropylene glycol, and mixtures thereof. In some cases, the polyol is propylene glycol. In some further cases, the polyol is one or both of propylene glycol and butylene glycol. Additionally, in some cases, the hair styling composition comprises at least propylene glycol, and optionally one or more polyols other than propylene glycol.

Non-limiting examples of polyols that may be included in the hair styling include and/or may be chosen from alkanediols such as glycerin, 1,2,6-hexanetriol, trimethylolpropane, ethylene glycol, propylene glycol, butylene glycol, pentylene glycol, hexylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, caprylyl glycol, 1,2-hexanediol, 1,2-pentanediol, and 4-methyl-1,2-pentanediol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, dipropylene glycol mono-iso-propyl ether, sorbitol, sorbitan, triacetin, and a mixture thereof.

The one or more polyols may, optionally, be glycols or glycol ethers such as, e.g., monomethyl, monoethyl and monobutyl ethers of ethylene glycol, propylene glycol or ethers thereof such as, e.g., monomethyl ether of propylene glycol, butylene glycol, hexylene glycol, dipropylene glycol as well as alkyl ethers of diethylene glycol, e.g., monoethyl ether or monobutyl ether of diethylene glycol. Preferably, the polyol is chosen from ethylene glycol, propylene glycol, butylene glycol, hexylene glycol, pentylene glycol, diethylene glycol, dipropylene glycol, 1,3 propanediol, glycerin, diglycerin, polyethylene glycols, and a mixture thereof.

Plant Based or Vegetable Based Oil(s)

The hair styling composition comprises a plant based or vegetable based oil(s), typically in an amount of 1 to 10 wt. %, based on the total weight of the hair styling composition. The amount of plant based or vegetable based oils present in the hair styling composition may be from about 1 to about 10 wt. %, about 1 to about 8 wt. %, about 1 to about 7 wt. %, about 1 to about 6 wt. %, about 1 to about 5 wt. %; about 2 to about 10 wt. %, about 2 to about 8 wt. %, about 2 to about 7 wt. %, about 2 to about 6 wt. %, about 2 to about 5 wt. %; about 3 to about 10 wt. %, about 3 to about 8 wt. %, about 3 to about 7 wt. %, about 3 to about 6 wt. %, about 3 to about 5 wt. %; about 4 to about 10 wt. %, about 4 to about 8 wt. %, about 4 to about 7 wt. %; about 5 to about 10 wt. %, about 5 to about 8 wt. %, or about 5 to about 7 wt. %, including all ranges and sub-ranges therebetween, based on the total weight of the hair styling composition.

Additionally and/or alternatively, the hair styling composition may exclude synthetic oils. In some case, the hair styling composition may exclude oils other than plant based and vegetable based oils. For example, the amount of synthetic oils and/or oils other than plant based and vegetable based oil may be about 5 wt. % or less, about 4 wt. % or less, about 3 wt. % or less, about 2 wt. % or less, about 1 wt. % or less, or about 0.5 wt. % or less, based on the total weight of the hair styling composition. In at least one embodiment, the hair styling composition is free of or essentially free of synthetic oils and/or oils other than plant based and vegetable based oil.

The plant based or vegetable based oils may be a hydrocarbon-based oil of plant origin and/or vegetable origin, Non-limiting examples of plant based or vegetable based oils include acai oil, almond oil, aloe vera oil, andiroba oil, annatto oil, avocado oil, babassu oil, borage oil, brazil nut oil, buriti oil, camelina oil, coffee oil, copaiba oil, emu oil, passion fruit oil, almond oil, castor oil, coconut oil, grapeseed oil, jojoba oil, macadamia nut oil, rose hip oil, ajwain oil, angelic root oil, anise oil, aragan oil, asafetida, balsam oil, basil oil, bay oil, bergamot oil, black pepper essential oil, buchu oil, birch oil, camphor, cannabis oil, caraway oil, cardamom seed oil, carrot seed oil, chamomile oil, calamus root oil, cinnamon oil, citronella oil, clary sage, clove leaf oil, coffee, coriander, costmary oil, cranberry seed oil, cubeb, cumin oil, cypress, cypriol, curry leaf, davana oil, dill oil, elecampane, eucalyptus oil, fennel seed oil, fenugreek oil, fir, frankincense oil, galangal, geranium oil, ginger oil, goldenrod, grapefruit oil, grapeseed oil, henna oil, helichrysum, horseradish oil, hyssop, Idaho tansy, jasmine oil, juniper berry oil, lavender oil, lemon oil, lemongrass, marjoram, melaleuca, lemon balm oil, mountain savory, mugwort oil, mustard oil, myrrh oil, myrtle, neem tree oil, neroli, nutmeg, orange oil, oregano oil, orris oil, palo santo, parsley oil, patchouli oil, perilla oil, pennyroyal oil, peppermint oil, petitgrain, pine oil, plum oil, ravensara, red cedar, roman chamomile, rose oil, rosehip oil, rosemary oil, rosewood oil, sandalwood oil, sassafras oil, savory oil, schisandra oil, spikenard, spruce, star anise oil, tangerine, tarragon oil, tea tree oil, thyme oil, tsuga oil, turmeric, valerian, vetiver oil, western red cedar, wintergreen, yarrow oil, ylang-ylang, and zedoary oil.

The plant based or vegetable based oil(s) may, in some cases, be a glyceride triesters, which are generally triesters of fatty acids and of glycerol, the fatty acids of which can have varied chain lengths from $C_4$ to $C_{24}$, it being possible for these chains to be saturated or unsaturated and linear or branched; these oils are in particular wheat germ oil, sunflower oil, grape seed oil, sesame oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin seed oil, marrow oil, blackcurrant oil, evening primrose oil, millet oil, barley oil, quinoa oil, rye oil, safflower oil, candlenut oil, passionflower oil, and musk rose oil.

In some instances, the plant based or vegetable based oil is an essential oil. For example, the plant based or vegetable based oil comprise sunflower oil, sesame oil, peppermint oil, macadamia nut oil, tea tree oil, evening primrose oil, sage oil, rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, ylang ylang, or a mixture thereof.

The plant based or vegetable based oil may comprise castor oil and/or shea butter. Preferably, the hair styling composition includes *Ricinus communis* (castor) seed oil, *Butyrospermum parkii* (shea) butter, and/or *Cocos nucifera* (coconut) oil.

Cationic Surfactant(s)

The hair styling composition includes a cationic surfactant(s). The amount of cationic surfactant(s) may be from about 0.1 to about 7 wt. % of the total weight of the hair styling composition. In some instances, the cationic surfactant(s) are in an amount ranging from about 0.1 to about 7 wt. %, about 0.1 to about 6 wt. %, about 0.1 to about 4 wt. %, about 0.1 to about 3 wt. %; about 0.2 to about 7 wt. %, about 0.2 to about 6 wt. %, about 0.2 to about 4 wt. %, about 0.2 to about 3 wt. %; about 0.5 to about 7 wt. %, about 0.5 to about 6 wt. %, about 0.5 to about 4 wt. %, about 0.5 to about 3 wt. %; about 1 to about 7 wt. %, about 1 to about 6 wt. %, about 1 to about 4 wt. %, about 1 to about 3 wt. %; about 1.5 to about 7 wt. %, about 1.5 to about 6 wt. %, about 1.5 to about 4 wt. %, about 1.5 to about 3 wt. %; about 2 to about 7 wt. %, about 2 to about 6 wt. %, about 2 to about 4 wt. %, or about 2 to about 3 wt. %, including ranges and sub-ranges therebetween, based on the total weight of the hair styling composition.

In at least one embodiment, the cationic surfactant in the hair styling composition is preferably behentrimonium chloride. In certain embodiments, the cationic surfactants include or are chosen from cetrimonium chloride, steartrimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, and mixtures thereof.

Additional, non-limiting examples of cationic surfactants include behenalkonium chloride, benzethonium chloride, cetylpyridinium chloride, lauralkonium chloride, cetalkonium chloride, cetrimonium bromide, cetrimonium chloride, cethylamine hydrofluoride, chlorallylmethenamine chloride (Quaternium-15), distearyldimonium chloride (Quaternium- 5), dodecyl dimethyl ethylbenzyl ammonium chloride (Quaternium-14), Quaternium-22, Quaternium-26, Quaternium-18 hectorite, dimethylaminoethylchloride hydrochloride, cysteine hydrochloride, diethanolammonium POE (10) oletyl ether phosphate, diethanolammonium POE (3)oleyl ether phosphate, tallow alkonium chloride, dimethyl dioctadecylammoniumbentonite, stearalkonium chloride, domiphen bromide, denatonium benzoate, myristalkonium chloride, laurtrimonium chloride, ethylenediamine dihydrochloride, guanidine hydrochloride, pyridoxine HCl, iofetamine hydrochloride, meglumine hydrochloride, methylbenzethonium chloride, myrtrimonium bromide, oleyltrimonium chloride, polyquaternium-1, procainehydrochloride, cocobetaine, stearalkonium bentonite, stearalkoniumhectonite, stearyl trihydroxyethyl propylenediamine dihydrofluoride, tallowtrimonium chloride, hexadecyltrimethyl ammonium bromide, and mixtures thereof.

The cationic surfactant(s) may also be chosen from optionally polyoxyalkylenated, primary, secondary or tertiary fatty amines, or salts thereof, and quaternary ammonium salts, and mixtures thereof. In some cases it is useful to use salts such as chloride salts of the quaternary ammonium compounds.

The fatty amines generally comprise at least one C5-C30 hydrocarbon-based chain. For example, quaternary ammonium salts, which may be incorporated in certain instances, include those corresponding to the following general formula:

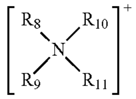

in which the groups $R_8$ to $R_{11}$, which may be identical or different, represent a linear or branched, saturated or unsaturated aliphatic group comprising from 1 to 30 carbon atoms, or an aromatic group such as aryl or alkylaryl, at least one of the groups $R_8$ to $R_{11}$ denoting a group comprising from 8 to 30 carbon atoms and preferably from 12 to 24 carbon atoms. The aliphatic groups may comprise heteroatoms especially such as oxygen, nitrogen, sulfur and halogens. The aliphatic groups are chosen, for example, from $C_1$-$C_{30}$ alkyl, $C_2$-$C_{30}$ alkenyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkyl acetate and $C_1$-$C_{30}$ hydroxyalkyl groups; $X^-$ is an anion chosen from the group of halides, phosphates, acetates, lactates, ($C_1$-$C_4$)alkyl sulfates, and ($C_1$-$C_4$)alkyl- or ($C_1$-$C_4$)alkylarylsulfonates.

Among the quaternary ammonium salts having a structure in accordance with the above general formula (III), those that are preferred are, on the one hand, tetraalkylammonium salts, for instance dialkyldimethylammonium or alkyltrimethylammonium salts in which the alkyl group contains approximately from 12 to 22 carbon atoms, such as behenyltrimethylammonium, distearyldimethylammonium, cetyltrimethylammonium or benzyldimethylstearylammonium salts, or, on the other hand, oleocetyldimethylhydroxyethylammonium salts, palmitylamidopropyltrimethylammonium salts, stearamidopropyltrimethylammonium salts and stearamidopropyldimethylcetearylammonium salts.

Examples of quaternary ammonium salt of imidazoline, which may be incorporated in certain instances, include those having a structure according to the general formula provided below:

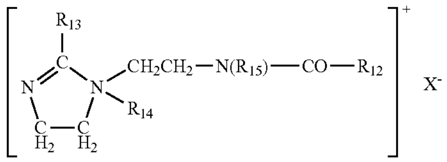

in which $R_{12}$ represents an alkenyl or alkyl group comprising from 8 to 30 carbon atoms, derived for example from tallow fatty acids, $R_{13}$ represents a hydrogen atom, a $C_1$-$C_4$ alkyl group or an alkyl or alkenyl group comprising from 8 to 30 carbon atoms, $R_{14}$ represents a $C_1$-$C_4$ alkyl group, $R_{15}$ represents a hydrogen atom or a C1-$C_4$ alkyl group, $X^-$ is an anion chosen from the group of halides, phosphates, acetates, lactates, alkyl sulfates, alkyl- or alkylarylsulfonates in which the alkyl and aryl groups preferably comprise, respectively, from 1 to 20 carbon atoms and from 6 to 30 carbon atoms. $R_{12}$ and $R_{13}$ preferably denote a mixture of alkenyl or alkyl groups containing from 12 to 21 carbon atoms, derived for example from tallow fatty acids, $R_{14}$ preferably denotes a methyl group, and $R_{15}$ preferably denotes a hydrogen atom. Such a product is sold, for example, under the name REWOQUAT W 75 by the company Rewo.

Examples of quaternary diammonium or triammonium salt, which may be incorporated in certain instances, include those having a structure in accordance with the following general formula:

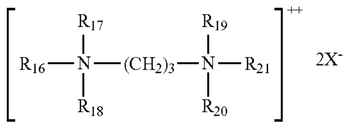

in which $R_{16}$ denotes an alkyl radical comprising approximately from 16 to 30 carbon atoms, which is optionally hydroxylated and/or interrupted with one or more oxygen atoms; $R_{17}$ is chosen from hydrogen or an alkyl radical comprising from 1 to 4 carbon atoms or a group ($R_{16a}$)($R_{17a}$)($R_{18a}$)N—$(CH_2)_3$, $R_{16a}$, $R_{17a}$, $R_{18a}$, $R_{18}$, $R_{19}$, $R_{20}$ and $R_{21}$, which may be identical or different, being chosen from hydrogen and an alkyl radical comprising from 1 to 4 carbon atoms; and $X^-$ is an anion chosen from the group of halides, acetates, phosphates, nitrates and methyl sulfates. Such compounds are, for example, Finquat CT-P, sold by the company Finetex (Quaternium 89), and Finquat CT, sold by the company Finetex (Quaternium 75), Examples of cationic/cationizable surfactants, which may be incorporated in certain instances, include those having a structure in accordance with the general formula provided below:

R4-A-R5-B wherein R4 is a saturated or unsaturated, straight or branched alkyl chain with 8 to 24 C atoms, R5 is a straight or branched alkyl chain with 1 to 4 C atoms, A is selected from:

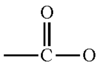 and 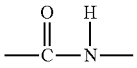

and B is selected from:

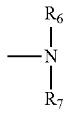

wherein $R_6$ and $R_7$ are the same or different and are H or an alkyl chain with 1 to 4 C atoms, hydroxyl alkyl chain with 1 to 4 C atoms and di hydroxyl alkyl chain with 2 to 4 C atoms,

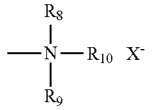

$R_8$ and $R_9$ are the same or different, an alkyl chain with 1 to 4 C atoms, hydroxyl alkyl chain with 1 to 4 C atoms and di hydroxyl alkyl chain with 2 to 4 C atoms, $R_{10}$ is an alkyl chain with 1 to 4 C atoms, hydroxyl alkyl chain with 1 to 4 C atoms or di hydroxyl alkyl chain with 2 to 4 C atoms.

In some instances, $R_4$ is saturated or unsaturated, straight or branched alkyl chain with 10 to 24C atoms, more preferably 12 to 22 C atoms and $R_5$ is straight or branched alkyl group with 1 to 4 C atoms, and A, B, $R_6$ to $R_{10}$ are same as above.

Non-limiting suitable examples are stearyloxypropyl amine, palmityloxypropyl amine, stearyloxypropyldimethyl amine, stearyloxypropyldiethyl amine, stearyloxyethylyldimethyl amine, stearyloxyethyl amine, myristyloxypropyl amine, myristyloxypropyldimethyl amine, palmitamidopropyl amine, palmitamidopropyl methylamine, palmitamidopropyl diethylamine, palmitamidopropyl dibutylamine, palmitamidopropyl buylamine, palmitamidopropyl dipropylamine, palmitamidopropyl propylamine, palmitamidopropyl dihydroxyethylamine, palmitamidopropyl hydroxyethylamine, palmitamidopropyl dihydroxypropylamine, palmitamidopropyl hydroxypropylamine, lauramidopropyl amine, lauramidopropyl methylamine, lauramidopropyl diethylamine, lauramidopropyl dibutylamine, lauramidopropyl buylamine, lauramidopropyl dipropylamine, lauramidopropyl propylamine, lauramidopropyl dihydroxyethylamine, lauramidopropyl hydroxyethylamine, lauramidopropyl dihydroxypropylamine, lauramidopropyl hydroxypropylamine, stearamidopropyl amine, stearamidopropyl dimethylamine, steara midopropyl diethylamine, stearamidopropyldibutylamine, stearamidopropyl butylamine, stearamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, behenamidopropyl amine, behenamidopropyl methylamine, behenamidopropyl diethylamine, behenamidopropyl dibutylamine, behenamidopropyl butylamine, behenamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, dipalmitamidopropyl methylamine, dipalmitamidopropyl ethylamine, dipalmitamidopropyl butylamine, dipalmitamidopropyl propylamine, dipalmitamidopropyl hydroxyethylamine, dipalmitamidopropyl hydroxypropylamine, dilauramidopropyl amine, dilauramidopropyl methylamine, dilauramidopropyl buylamine, dilauramidopropyl hydroxyethylamine, dilauramidopropyl hydroxypropylamine, distearamidopropyl amine, distearamidopropyl methylamine, dibehenamidopropyl propylamine, dibehenamidopropyl hydroxyethylamine, palmitoamidopropyl trimethyl ammonium chloride, stearamidopropyl trimethylammonium chloride, behenamidopropyl tri hydroxyethalmonium chloride, distearylamidopropyl dimethyl ammonium chloride, dicetylamidodihydroxyethyl ammonium chloride, palmitoylpropyl amine, palmitoylpropyl methylamine, palmitoylpropyl diethylamine, palmitoylpropyl dibutylamine, palmitoylpropyl buylamine, palmitoylpropyl dipropylamine, palmitoylpropyl propylamine, palmitoylpropyl dihydroxyethylamine, palmitoylpropyl hydroxyethylamine, palmitoylpropyl dihydroxypropylamine, palmitoylpropyl hydroxypropylamine, myristoylpropyl amine, myristoylpropyl methylamine, myristoylpropyl diethylamine, myristoylpropyl dibutylamine, myristoylpropyl buylamine, myristoylpropyl dipropylamine, myristoylpropyl propylamine, myristoylpropyl dihydroxyethylamine, myristoylpropyl hydroxyethylamine, myristoylpropyl dihydroxypropylamine, myristoylpropyl hydroxypropylamine, stearoylpropyl amine, stearoylpropyl methylamine, stearoylpropyl diethylamine, stearoylpropyl dibutylamine, stearoylpropyl butylamine, stearoylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, behenylpropyl amine, behenylpropyl methylamine, behenylpropyl diethylamine, behenylpropyl dibutylamine, behenylpropyl butylamine, behenylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, dipalmitoylpropyl methylamine, dipalmitoylpropyl ethylamine, dipalmitylpropyl butylamine, dipalmitylpropyl propylamine, dipalmitylpropyl hydroxyethylamine, dipalmitylpropyl hydroxypropylamine, dilauroylpropyl amine, dilauroylpropyl methylamine, dilauroylpropyl buylamine, dilauroylpropyl hydroxyethylamine, dilauroylpropyl hydroxypropylamine, distearylpropyl amine, distearylpropyl methylamine, dibehenylpropyl propylamine, dibehenylpropyl hydroxyethylamine, palmitylpropyl trimethyl ammonium chloride, stearylpropyl trimethylammonium chloride, behenylpropyl tri hydroxyethalmonium chloride, distearylpropyl dimethyl ammonium chloride, dicetyldihydroxyethyl ammonium chloride, dioleoylethylhydroxyethylmonium methosulfate, and dicocoylethylhydroxyethylmonium methosulfate.

Cationizable surfactants may be chosen from fatty alkylamines, preferably, fatty dialkylamines. Non-limiting examples include dimethyl lauramine, dimethyl behenamine, dimethyl cocamine, dimethyl myristamine, dimethyl palmitamine, dimethyl stearamine, dimethyl tallowamine, dimethyl soyamine, and mixtures thereof.

Fatty dialkylamines include fatty amidoamine compounds, their salts, and mixtures thereof. Non-limiting examples include oleamidopropyl dimethylamine, linoleamidopropyl dimethylamine, isostearamidopropyl dimethylamine, stearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, and palmitamidopropyl dimethylamine.

Non-polymeric, mono-, di-, and/or tri-carboxylic acids may be used to "neutralize" the fatty dialkylamines. In some cases, the one or more non-polymeric, mono-, di-, and/or tri-carboxylic acids include at least one dicarboxylic acid. Non-limiting examples include lactic acid, oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, benzoic acid, and mixtures thereof. In particular, lactic acid or tartaric acid or mixtures thereof are useful, especially in combination with fatty dimethylamines such as, for example, stearamidopropyl dimethylamine.

In an embodiment, hair styling composition may be formulated with a cationic surfactant chosen from behentrimonium chloride, cetrimonium chloride, behentrimonium methosulfate, or mixtures thereof.

The hair styling composition may be formulated such that the two or more cationic surfactants are associated with the same or different balancing anionic ions. For example, at least one of the two or more cationic surfactants may have a chloride ion and/or a sulfate ion. In some instances, the two or more cationic surfactants comprise cetrimonium chloride and one or both of behentrimonium methosulfate and behentrimonium chloride. In further instances, the two or more cationic surfactants comprise behentrimonium chloride and one or both of behentrimonium methosulfate and cetrimonium chloride.

Emulsifier(s)

The hair styling composition includes at least emulsifiers chosen from glyceryl ester, a fatty alcohol, and a mixture thereof. Preferably, the emulsifiers of the hair styling compositions include a glyceryl ester and a fatty alcohol. In some cases, the emulsifiers further comprise a non-glyceryl ester, such as fatty ester. Additionally or alternatively, the emulsifiers may comprise one or more glucoside.

The total amount of emulsifiers in the hair styling composition may be about 0.5 to about 10 wt. %, based on the total weight of the hair styling composition. For example, the emulsifiers may be present in an amount of about 0.5 to about 10 wt. %, about 0.5 to about 8 wt. %, about 0.5 to about 7 wt. %, about 0.5 to about 6 wt. %, about 0.5 to about 5 wt. %; about 1 to about 10 wt. %, about 1 to about 8 wt. %, about 1 to about 7 wt. %, about 1 to about 6 wt. %, about 1 to about 5 wt. %; about 2 to about 10 wt. %, about 2 to about 8 wt. %, about 2 to about 7 wt. %, about 2 to about 6 wt. %, about 2 to about 5 wt. %; about 3 to about 10 wt. %, about 3 to about 8 wt. %, about 3 to about 7 wt. %, about 3 to about 6 wt. %, about 3 to about 5 wt. %; about 4 to about 10 wt. %, about 4 to about 8 wt. %, about 4 to about 7 wt. %; about 5 to about 10 wt. %, about 5 to about 8 wt. %, or about 5 to about 7 wt. %, including all ranges and sub-ranges therebetween, based on the total weight of the hair styling composition.

(i) Glyceryl Ester(s)

The emulsifiers typically comprise one or more glyceryl ester. The glyceryl esters may have a carbon chain of 8 to 24 carbons. The glyceryl ester may be chosen from:

esters of an oligomeric glycerol, especially the esters of diglycerol, in particular the condensates of adipic acid and of glycerol, for which a portion of the hydroxyl groups of the glycerols have reacted with a mixture of fatty acids, such as steric acid, capric acid, stearic and isostearic acid and 12-hydroxystearic acid, such as, in particular, those sold under the trade mark SOFTISAN 649 by the company Cremer Oleo or under the trademark SP SUPERMOL B MBAL-SS-(RB) by the company Croda, such as bis-diglyceryl polyacyladipate-2;

the arachidyl propionate sold under the trade mark WAXENOL 801 by Alzo, phytosterol esters, triglycerides of fatty acids and derivatives thereof, such as hydrogenated cocoglycerides;

noncrosslinked polyesters resulting from the poly condensation between a linear or branched C4-C50 dicarboxylic acid or polycarboxylic acid and a C2-C50 diol or polyol;

aliphatic esters of an ester resulting from the esterification of an aliphatic hydroxycarboxylic acid ester with an aliphatic carboxylic acid; or a mixture thereof.

The glycerol ester may be a polyglycerol esters of fatty acids (polygylceryl esters) having a structure in accordance with the following formula:

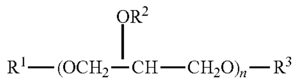

wherein n is from 2 to 20 or from 2 to 10 or from 2 to 5, or is 2, 3, 4, 5, 6, 7, 8, 9, or 10, and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$. Additionally, non-limiting examples of nonionic polyglycerol esters of fatty acids include polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, and mixtures thereof.

The glyceryl ester may be chosen from esters of an oligomeric glycerol, arachidyl propionate, phytosterol esters, triglycerides of fatty acids and derivatives thereof, noncrosslinked polyesters resulting from the poly condensation between a linear or branched C4-C50 dicarboxylic acid or polycarboxylic acid and a C2-C50 diol or polyol, aliphatic esters of an ester resulting from the esterification of an aliphatic hydroxycarboxylic acid ester with an aliphatic carboxylic acid, and a mixture thereof. Non-limiting examples of glyceryl esters include bis-diglyceryl polyacyladipate-2, glyceryl behenate, glyceryl caprate, glyceryl cocoate, glyceryl erucate, glyceryl hydroxystearate, glyceryl isostearate, glyceryl lanolate, glyceryl laurate, glyceryl linoleate, glyceryl myristate, glyceryl oleate, glyceryl palmitate lactate, glyceryl sesquioleate, glyceryl stearate, glyceryl stearate citrate, glyceryl stearate lactate, glyceryl dioleate, glyceryl distearate, glyceryl laurate, or a mixture thereof. In at least one instance the glyceryl ester comprises glyceryl stearate, bis-diglyceryl polyacyladipate, or a mixture thereof. In at least one other instance, the glyceryl ester comprises bis-diglyceryl polyacyladipate-2 and optionally, a second glyceryl ester. In at least one other instance, the glyceryl ester comprises glyceryl stearate, and optionally, a second glyceryl ester.

In an some cases, the glyceryl ester is present in an amount of about 0.1 to about 9.8 wt. %, about 0.1 to about 8 wt. %, about 0.1 to about 7 wt. %, about 0.1 to about 6 wt. %, about 0.1 to about 5 wt. %; about 0.5 to about 9.8 wt. %, about 0.5 to about 8 wt. %, about 0.5 to about 7 wt. %, about 0.5 to about 6 wt. %, about 0.5 to about 5 wt. %; about 1 to about 9.8 wt. %, about 1 to about 8 wt. %, about 1 to about 7 wt. %, about 1 to about 6 wt. %, about 1 to about 5 wt. %; about 2 to about 9.8 wt. %, about 2 to about 8 wt. %, about 2 to about 7 wt. %, about 2 to about 6 wt. %, about 2 to about 5 wt. %; about 3 to about 9.8 wt. %, about 3 to about 8 wt. %, about 3 to about 7 wt. %, about 3 to about 6 wt. %, about 3 to about 5 wt. %; about 4 to about 9.8 wt. %, about 4 to about 8 wt. %, about 4 to about 7 wt. %; about 5 to about 9.8 wt. %, about 5 to about 8 wt. %, or about 5 to about 7 wt. %, including all ranges and sub-ranges therebetween, based on the total weight of the hair styling composition.

(ii) Fatty Alcohol(s)

The emulsifiers of the hair styling composition typically include one or more fatty alcohol(s). Suitable fatty alcohols include those having a fatty group with a carbon chain of greater than 8 carbon atoms, such as 8 to 50 carbon atoms, 8 to 40 carbon atoms, 8 to 30 carbon atoms, 8 to 22 carbon atoms, 12 to 22 carbon atoms, or 12 to 18 carbon atoms, including all ranges and subranges therebetween. In some instances, the fatty group of the fatty alcohols has a carbon chain of 10 to 20 carbon atoms or 10 to 18 carbon atoms. The fatty alcohols may be chosen from polyethylene glycol ethers, such as those having a fatty alcohol group with a carbon chain of 12 to 16 or 12 to 14 carbon atoms.

The fatty alcohol portion is preferably hydrogenated (for example, stearyl, lauryl, cetyl, cetearyl); however, the fatty alcohol may contain one or more double bonds (for example, oleyl). Non-limiting examples of fatty alcohols include decyl alcohol, undecyl alcohol, dodecyl alcohol, myristyl alcohol, lauryl alcohol, cetyl alcohol, stearyl alcohol, cetearyl alcohol (cetyl alcohol and stearyl alcohol), isostearyl alcohol, isocetyl alcohol, behenyl alcohol, linalool, oleyl alcohol, cis-4-t-butylcyclohexanol, isotridecyl alcohol, myricyl alcohol, and a mixture thereof. In some cases, the fatty alcohols comprise at least one of or may be chosen from myristyl alcohol, lauryl alcohol, cetyl alcohol, stearyl alcohol, cetearyl alcohol, isostearyl alcohol, oleyl alcohol, isotridecyl alcohol, and a mixture thereof.

The fatty alcohol may be saturated or unsaturated. Exemplary saturated liquid fatty alcohols may be branched and optionally contain in their structure at least one aromatic or non-aromatic ring. In some instances, however, the fatty alcohols are acyclic. Non-limiting examples of liquid saturated fatty alcohols include octyldodecanol, isostearyl alcohol, and 2-hexyldecanol.

Exemplary unsaturated liquid fatty alcohol may include in their structure at least one double or triple bond. For example, the fatty alcohols may include several double bonds (such as 2 or 3 double bond), which may be conjugated or non-conjugated. The unsaturated fatty alcohols can be linear or branched and may be acyclic or include in their structure at least one aromatic or non-aromatic ring. Liquid unsaturated fatty alcohols may include or be chosen from oleyl alcohol, linoleyl alcohol, linolenyl alcohol and undecylenyl alcohol.

The fatty alcohols may be alkoxylated fatty alcohols, e.g., having about 1 to about 100 moles of an alkylene oxide per mole of alkoxylated fatty alcohol. For example, the alkoxylated fatty alcohols may be alkoxylated with about 1 to about 80 moles, about 2 to about 50, about 5 to about 45 moles, about 10 to about 40 moles, or 15 to about 35 mores, including all ranges and subranges therebetween, of an alkylene oxide per mole of alkoxylated fatty alcohol.

As examples of alkoxylated fatty alcohols, steareth (for example, steareth-2, steareth-20, and steareth-21), laureth (for example, laureth-4, and laureth-12), ceteth (for example, ceteth-10 and ceteth-20) and ceteareth (for example, ceteareth-2, ceteareth-10, and ceteareth-20) are mentioned. In at least one instance, the one or more alkoxylated fatty alcohols include steareth-20. In some instances, the one or more alkoxylated fatty alcohols may be exclusively steareth-20.

Additional fatty alcohol derivatives that may, optionally be suitable include methyl stearyl ether; 2-ethylhexyl dodecyl ether; stearyl acetate; cetyl propionate; the ceteth series of compounds, such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; $C_1$-$C_{30}$ alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof.

In some embodiments, the fatty alcohol is selected from cetearyl alcohol, cetyl alcohol, stearyl alcohol, behenyl alcohol, arachidyl alcohol, eicosyl alcohol, myristyl alcohol, 2-dodecylhexadecanol, 2-tetradecyl-1-octadecanol, 2-tetradecyl-1-eicosanol, 2-hexadecyl-1-octadecanol, 2-hexadecyl-1-eicosanol, and a mixture thereof. Preferably, the fatty alcohol is selected from cetearyl alcohol, cetyl alcohol, stearyl alcohol, and a mixture thereof.

In an some cases, the fatty alcohol is present in an amount of about 0.1 to about 9.8 wt. %, about 0.1 to about 8 wt. %, about 0.1 to about 7 wt. %, about 0.1 to about 6 wt. %, about 0.1 to about 5 wt. %; about 0.5 to about 9.8 wt. %, about 0.5 to about 8 wt. %, about 0.5 to about 7 wt. %, about 0.5 to about 6 wt. %, about 0.5 to about 5 wt. %; about 1 to about 9.8 wt. %, about 1 to about 8 wt. %, about 1 to about 7 wt. %, about 1 to about 6 wt. %, about 1 to about 5 wt. %; about 2 to about 9.8 wt. %, about 2 to about 8 wt. %, about 2 to about 7 wt. %, about 2 to about 6 wt. %, about 2 to about 5 wt. %; about 3 to about 9.8 wt. %, about 3 to about 8 wt. %, about 3 to about 7 wt. %, about 3 to about 6 wt. %, about 3 to about 5 wt. %; about 4 to about 9.8 wt. %, about 4 to about 8 wt. %, about 4 to about 7 wt. %; about 5 to about 9.8 wt. %, about 5 to about 8 wt. %, or about 5 to about 7 wt. %, including all ranges and sub-ranges therebetween, based on the total weight of the hair styling composition.

(iii) Ester(s) that is not Glyceryl Ester(s)

The hair styling compositions may include an ester other than glyceryl esters. In some cases, the ester other than glyceryl ester is isopropyl esters, cetyl esters, or a mixture thereof. Non-limiting examples of isopropyl esters are isopropyl myristate, isopropyl laurate, isopropyl oleate, isopropyl palmitate, and isopropyl stearate. The ester that is not a glyceryl ester may be selected from isopropyl myristate, cetyl esters, isopropyl palmitate, or a mixture thereof.

The ester other than glyceryl ester may be chosen from a fatty ester. Examples of ethoxylated fatty esters that may be mentioned include the adducts of ethylene oxide with esters of lauric acid, palmitic acid, stearic acid or behenic acid, and mixtures thereof, especially those containing from 9 to 100 oxyethylene groups, such as PEG-9 to PEG-50 laurate (as the INCI names: PEG-9 laurate to PEG-50 laurate); PEG-9 to PEG-50 palmitate (as the INCI names: PEG-9 palmitate to PEG-50 palmitate); PEG-9 to PEG-50 stearate (as the INCI names: PEG-9 stearate to PEG-50 stearate); PEG-9 to PEG-50 palmitostearate; PEG-9 to PEG-50 behenate (as the INCI names: PEG-9 behenate to PEG-50 behenate); polyethylene glycol 100 EO monostearate (INCI name: PEG-100 stearate); and mixtures thereof.

The fatty alcohol is present in an amount of about 0.1 to about 9.8 wt. %, about 0.1 to about 8 wt. %, about 0.1 to about 7 wt. %, about 0.1 to about 6 wt. %, about 0.1 to about 5 wt. %; about 0.5 to about 9.8 wt. %, about 0.5 to about 8 wt. %, about 0.5 to about 7 wt. %, about 0.5 to about 6 wt. %, about 0.5 to about 5 wt. %; about 1 to about 9.8 wt. %, about 1 to about 8 wt. %, about 1 to about 7 wt. %, about 1 to about 6 wt. %, about 1 to about 5 wt. %; about 2 to about 9.8 wt. %, about 2 to about 8 wt. %, about 2 to about 7 wt. %, about 2 to about 6 wt. %, about 2 to about 5 wt. %; about 3 to about 9.8 wt. %, about 3 to about 8 wt. %, about 3 to about 7 wt. %, about 3 to about 6 wt. %, about 3 to about 5 wt. %; about 4 to about 9.8 wt. %, about 4 to about 8 wt. %, about 4 to about 7 wt. %; about 5 to about 9.8 wt. %, about 5 to about 8 wt. %, or about 5 to about 7 wt. %, including all ranges and sub-ranges therebetween, based on the total weight of the hair styling composition.

(iv) Glucoside(s)

The glycoside may be an alkylpolyglucoside, such as those having a structure in accordance with the following formula:

$$R1\text{-}O\text{—}(R2O)n\text{-}Z(x) \qquad (I)$$

wherein:

R1 is an alkyl group having 8-18 carbon atoms;

R2 is an ethylene or propylene group;

Z is a saccharide group with 5-6 carbon atoms;

n is an integer ranging from 0 to 10; and x is an integer ranging from 1 to 5.

Non-limiting examples of alkylpolyglucosides that may be incorporated into the hair styling composition include those chosen from arachidyl glucoside, $C_{12-20}$ alkyl glucoside, caprylyl/capryl glucoside, cetearyl glucoside, coco-glucoside, lauryl glucoside, decyl glucoside, sodium lauryl glucose carboxylate, and a mixture thereof. In some cases, the alkyl polyglucoside compound is selected from the group consisting of cetearyl glucoside, lauryl glucoside, decyl glucoside, coco glucoside, and a mixture thereof. In at least one instance, the glucoside is cetearyl glucoside.

The glucoside is present in an amount of about 0.1 to about 9.8 wt. %, about 0.1 to about 8 wt. %, about 0.1 to about 7 wt. %, about 0.1 to about 6 wt. %, about 0.1 to about 5 wt. %; about 0.5 to about 9.8 wt. %, about 0.5 to about 8 wt. %, about 0.5 to about 7 wt. %, about 0.5 to about 6 wt. %, about 0.5 to about 5 wt. %; about 1 to about 9.8 wt. %, about 1 to about 8 wt. %, about 1 to about 7 wt. %, about 1 to about 6 wt. %, about 1 to about 5 wt. %; about 2 to about 9.8 wt. %, about 2 to about 8 wt. %, about 2 to about 7 wt. %, about 2 to about 6 wt. %, about 2 to about 5 wt. %; about 3 to about 9.8 wt. %, about 3 to about 8 wt. %, about 3 to about 7 wt. %, about 3 to about 6 wt. %, about 3 to about 5 wt. %; about 4 to about 9.8 wt. %, about 4 to about 8 wt. %, about 4 to about 7 wt. %; about 5 to about 9.8 wt. %, about 5 to about 8 wt. %, or about 5 to about 7 wt. %, including all ranges and sub-ranges therebetween, based on the total weight of the hair styling composition.

Thickening Agent(s)

The hair styling compositions described herein may, optionally, include a thickener. The thickening agent may be in an amount of about 0.01 wt. % to about 10 wt. %, about 0.01 wt. % to about 8 wt. %, about 0.01 wt. % to about 6 wt. %, about 0.01 wt. % to about 5 wt. %, about 0.01 wt. % to about 4 wt. %, about 0.01 wt. % to about 3 wt. %, about 0.01 wt. % to about 2 wt. %, about 0.01 wt. % to about 1 wt. %; about 0.05 wt. % to about 10 wt. %, about 0.05 wt. % to about 8 wt. %, about 0.05 wt. % to about 6 wt. %, about 0.05 wt. % to about 5 wt. %, about 0.05 wt. % to about 4 wt. %, 0.05 wt. % to about 3 wt. %, about 0.05 wt. % to about 2 wt. %, about 0.05 wt. % to about 1 wt. %; about 0.1 wt. % to about 10 wt. %, about 0.1 wt. % to about 8 wt. %, about 0.1 wt. % to about 6 wt. %, about 0.1 wt. % to about 5 wt. %, about 0.1 wt. % to about 4 wt. %, about 0.1 wt. % to about 3 wt. %, about 0.1 wt. % to about 2 wt. %, about 0.1 wt. % to about 1 wt. %; about 0.2 wt. % to about 10 wt. %, about 0.2 wt. % to about 8 wt. %, about 0.2 wt. % to about 6 wt. %, about 0.2 wt. % to about 5 wt. %, about 0.2 wt. % to about 4 wt. %, about 0.2 wt. % to about 3 wt. %, about 0.2 wt. % to about 2 wt. %, about 0.2 wt. % to about 1 wt. %; about 0.3 wt. % to about 10 wt. %, about 0.3 wt. % to about 8 wt. %, about 0.3 wt. % to about 6 wt. %, about 0.3 wt. % to about 5 wt. %, about 0.3 wt. % to about 4 wt. %, about 0.3 wt. % to about 3 wt. %, about 0.3 wt. % to about 2 wt. %, or about 0.3 wt. % to about 1 wt. %, including ranges and subranges thereof, based on the total weight of the hair styling composition. Further, the amount of thickening agent may be from 0.1, 0.2, 0.3, 0.4, 0.5, 0.6, 0.7, 0.8, 0.9, 1.0, or 1.5 wt. % to 2, 3, 4, or 5 wt. %, including ranges and subranges thereof, based on the total weight of the hair styling composition.

Many thickening agents are water-soluble, and increase the viscosity of water or form an aqueous gel when the hair styling composition of the invention is dispersed/dissolved in water. The aqueous solution may be heated and cooled, or neutralized, for forming the gel, if necessary. The thickening agent may be dispersed/dissolved in an aqueous solvent that is soluble in water, e.g., ethyl alcohol when it is dispersed/dissolved in water.

Thickening agents may be referred to as "thickeners" or "viscosity modifying agents." Thickening agents are typically included to increase the viscosity of the compositions. Nonetheless, in some instances, certain thickening agents provide additional, surprising benefits to the compositions. Non-limiting examples of thickening agents include polyacrylate crosspolymers (such as, sodium polyacrylate) or crosslinked polyacrylate polymers (such as, crosslinked sodium polyacrylate), cationic acrylate copolymers, anionic acrylic or carboxylic acid polymers, polyacrylamide polymers, polysaccharides such as cellulose derivatives, gums, polyquaterniums, vinylpyrrolidone homopolymers/copolymers, $C_{8-24}$ hydroxyl substituted aliphatic acid, $C_{8-24}$ conjugated aliphatic acid, sugar fatty esters, polyglyceryl esters, and a mixture thereof. Suitable thickeners may be found in U.S. patent application Ser. No. 16/731,654, which is incorporated herein, in its entirety for all purposes.

The thickening agents may be chosen from xanthan gum, guar gum, biosaccharide gum, cellulose, acacia seneca gum, sclerotium gum, agarose, pechtin, gellan gum, hyaluronic acid. Additionally, the thickening agents may include polymeric thickeners selected from the group consisting of ammonium polyacryloyldimethyl taurate, ammonium acryloyldimethyltaurate/VP copolymer, acrylates copolymers, polyacrylamide, carbomer, and acrylates/$C_{10-30}$ alkyl acrylate crosspolymer. In one instance, the thickening agent comprises sodium polyacrylate.

Particular types of thickening agents that may be mentioned include the following:

Carboxylic Acid or Carboxylate Based Homopolymer or Co-Polymer, which can be Linear or Crosslinked These polymers contain one or more monomers derived from acrylic acid, substituted acrylic acids, and salts and esters of these acrylic acids (acrylates) and the substituted acrylic acids. Commercially available polymers include those sold under the trade names CARBOPOL, ACRYSOL, POLYGEL, SOKALAN, CARBOPOL ULTREZ, and POLYGEL. Examples of commercially available carboxylic acid polymers include the carbomers, which are homopolymers of acrylic acid crosslinked with allyl ethers of sucrose or pentaerytritol. The carbomers are available as the CARBOPOL 900 series from B.F. Goodrich (e.g., CARBOPOL 954). In addition, other suitable carboxylic acid polymeric agents include ULTREZ 10 (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as CARBOPOL 1342, CARBOPOL 1382, PEMULEN TR-1, and PEMULEN TR-2, from B.F. Goodrich.

Other suitable carboxylic acid or carboxylate polymeric agents include copolymers of acrylic acid and alkyl C5-C10 acrylate, copolymers of acrylic acid and maleic anhydride, and polyacrylate crosspolymer-6. Polyacrylate Crosspolymer-6 is available in the raw material known as SEPIMAX ZEN from Seppic.

Another suitable carboxylic acid or carboxylate polymeric agent includes acrylamidopropyltrimonium chloride/acrylates copolymer, a cationic acrylates copolymer (or a quaternary ammonium compound), available as a raw material known under the tradename of SIMULQUAT HC 305 from Seppic.

In certain embodiments, the carboxylic acid or carboxylate polymer thickeners useful herein are those selected from carbomers, acrylates/C10-C30 alkyl acrylate crosspolymers, polyacrylate crosspolymer-6, acrylamidopropyltrimonium chloride/acrylates copolymer, and mixtures thereof.

Polyquaternium Compounds

Non-limiting examples, include polyquaternium-1, polyquaternium-2, polyquaternium-3, polyquaternium-4, polyquaternium-5, polyquaternium-6, polyquaternium-7, polyquaternium-8, polyquaternium-9, polyquaternium-10, polyquaternium-11, polyquaternium-12, polyquaternium-13, polyquaternium-14, polyquaternium-15, polyquaternium-16, polyquaternium-17, polyquaternium-18, polyquaternium-19, polyquaternium-20, polyquaternium-21, polyquaternium-22, polyquaternium-23, polyquaternium-24, polyquaternium-25, polyquaternium-26, polyquaternium-27, polyquaternium-28, polyquaternium-29, polyquaternium-30, polyquaternium-40, polyquaternium-41, polyquaternium-42, polyquaternium-43, polyquaternium-44, polyquaternium-45, polyquaternium-46, polyquaternium-47, polyquaternium-48, polyquaternium-49, polyquaternium-50, polyquaternium-51, polyquaternium-52, polyquaternium-53, polyquaternium-54, polyquaternium-55, polyquaternium-56, polyquaternium-57, polyquaternium-58, polyquaternium-59, polyquaternium-60, polyquaternium-61, polyquaternium-62, polyquaternium-63, polyquaternium-64, polyquaternium-65, polyquaternium-66, polyquaternium-67, etc. In some cases, preferred polyquaternium compounds include polyquaternium-10, polyquaternium-11, polyquaternium-67, and a mixture thereof. In some instances, the hair styling compositions include polyquaternium-10, polyquaternium-11, polyquaternium-67, or a mixture thereof.

Celluloses

Non-limiting examples of celluloses include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. In some instances, the cellulose is selected from water-soluble cellulose derivatives (for example, carboxymethyl cellulose, methyl cellulose, methylhydroxypropyl cellulose, hydroxyethyl cellulose, hydroxypropyl cellulose, cellulose sulfate sodium salt). Furthermore, in some instance, the cellulose is preferably hydroxypropylcellulose (HPC). In some instances, the hair styling compositions include one or more cellulose thickeners (e.g., microcrystalline cellulose, carboxymethylcellulose, hydroxymethylcellulose, and hydroxypropylcellulose).

Polyvinylpyrrolidone (PVP) and Co-Polymers

Non-limiting examples include Polyvinylpyrrolidone (PVP), Polyvinylpyrrolidone (PVP)/vinyl acetate copolymer (PVP/VA copolymer), polyvinylpyrrolidone (PVP)/eicosene copolymer, PVP/hexadecene copolymer, etc. Commercially available polyvinylpyrrolidone includes LUVISKOL K30, K85, K90 available from BASF. Commercially available copolymers of vinylpyrrolidone and vinylacetate include LUVISKOL VA37, VA64 available from BASF; copolymers of vinylpyrrolidone, methacrylamide, and vinylimidazole (INCI: VP/Methacrylamide/Vinyl Imidazole Copolymer) is commercially available as LUVISET from BASF. In some instances, PVP and PVP/VA copolymer are preferred.

Sucrose Esters

Non-limiting examples include sucrose palmitate, sucrose cocoate, sucrose monooctanoate, sucrose monodecanoate, sucrose mono- or dilaurate, sucrose monomyristate, sucrose mono- or dipalmitate, sucrose mono- and distearate, sucrose mono-, di- or trioleate, sucrose mono- or dilinoleate, sucrose pentaoleate, sucrose hexaoleate, sucrose heptaoleate or sucrose octooleate, and mixed esters, such as sucrose palmitate/stearate, and mixtures thereof.

Polyglyceryl Esters

Non-limiting polyglycerol esters of fatty acids (polyglyceryl esters) include those of the following formula:

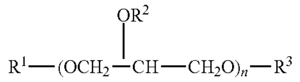

wherein n is from 2 to 20 or from 2 to 10 or from 2 to 5, or is 2, 3, 4, 5, 6, 7, 8, 9, or 10, and R1, R2 and R3 each may independently be a fatty acid moiety or hydrogen, provided that at least one of R1, R2, and R3 is a fatty acid moiety. For instance, R1, R2 and R3 may be saturated or unsaturated, straight or branched, and have a length of C1-C40, C1-C30, C1-C25, or C1-C20, C1-C16, or C1-C10. Additionally, non-limiting examples of nonionic polyglycerol esters of fatty acids include polyglyceryl-4 caprylate/caprate, polyglyceryl-10 caprylate/caprate, polyglyceryl-4 caprate, polyglyceryl-10 caprate, polyglyceryl-4 laurate, polyglyceryl-5 laurate, polyglyceryl-6 laurate, polyglyceryl-10 laurate, polyglyceryl-10 cocoate, polyglyceryl-10 myristate, polyglyceryl-10 oleate, polyglyceryl-10 stearate, and mixtures thereof.

C8-24 Hydroxyl Substituted Aliphatic Acid and C8-24 Conjugated Aliphatic Acid Non-limiting examples include conjugated linoleic acid, cis-parinaric acid, trans-7-octadecenoic acid, cis-5,8,11,14,17-eicosapentanoic acid, cis-4,7,10,13,16,19-docosahexenoic acid, columbinic acid, linolenelaidic acid, ricinolaidic acid, stearidonic acid, 2-hydroxystearic acid, alpha-linolenic acid, arachidonic acid, cis-11,14-eicosadienoic acid, linolelaidic acid, monopetroselinic acid, petroselinic acid, ricinoleic acid, trans-vaccenic acid, cis-11,14,17-eicosatrienoic acid, cis-5-eicosenoic acid, cis-8,11,14-eicosatrienoic acid, hexadecatrienoic acid, palmitoleic acid, petroselaidic acid, trans farnesol, cis-13,16-docosadienoic acid, cis-vaccenic acid, cis-11-eicosenoic acid, cis-13,16,19-docosatrienoic acid, cis-13-octadecenoic acid, cis-15-octadecanoic acid, cis-7,10,13,16 docosatetraenoic acid, elaidic acid, gamma-linolenic acid, geranic acid, geranyl geranoic acid, linoleic acid, oleic acid, pinolenic acid, trans-13-octadecenoic acid. More preferably, the aliphatic acid comprises 12-hydroxystearic acid, conjugated linoleic acid, or a mixture thereof.

Gums

Non-limiting examples of gums include gum arabic, tragacanth gum, karaya gum, guar gum, gellan gum, tara gum, locust bean gum, tamarind gum, xanthan gum, locust bean gum, seneca gum, sclerotium gum, etc.

pH Adjuster(s)

The hair styling composition may include one or more pH adjusters to increase or decrease the overall pH of the hair styling composition. For example, one or more acids may be included to decrease the pH of the hair styling composition. Examples of suitable acids for decreasing the pH of the hair styling composition include, but are not limited to, citric acid, acetic acid, and the like. The hair styling composition may include one or more bases, such as sodium hydroxide, potassium hydroxide and the like, to decrease the pH of the hair styling composition. Additional or alternative acids and bases that are suitable for adjusting the pH of the hair styling composition are readily known to one of ordinary skill in the art.

The hair styling composition may, desirably, have a pH of about 4 to about 7, preferably about 4.5 to about 6.5 or about 5.5 to about 6.5. In one instance, the pH of the hair styling composition is 6 or about 6. The amount of the pH adjuster in the hair styling composition may be based on the desired pH of the final hair styling composition and/or product. For example, the total amount of the pH adjuster may range from about 0.05 to about 20 wt. %, based on the total weight of the composition. In some instances, the total amount of pH adjuster is from about 0.05 to about 15 wt. %, about 0.5 to about 10 wt. %, about 1 to about 5 wt. %, about 1.5 to about 4 wt. %, or about 2.0 to about 3 wt. %, including ranges and sub-ranges therebetween, based on the total weight of the composition.

Water

The total amount of water in the hair styling composition can vary, but is typically about 50 to about 95 wt. %, based on the total weight of the hair styling composition. In some instances, total amount of water is about 50 to about 90 wt. %, about 50 to about 85 wt. %, about 50 to about 80 wt. %; about 55 to about 95 wt. %, about 55 to about 90 wt. %, about 55 to about 85 wt. %, about 55 to about 80 wt. %; about 60 to about 95 wt. %, about 60 to about 90 wt. %, about 60 to about 85 wt. %, about 60 to about 80 wt. %; about 65 to about 95 wt. %, about 65 to about 90 wt. %, about 65 to about 85 wt. %, or about 65 to about 80 wt. %; about 70 to about 95 wt. %, about 70 to about 90 wt. %, about 70 to about 85 wt. %, about 70 to about 80 wt. %, including ranges and subranges therebetween, based on the total weight of the hair styling composition.

METHODS OF USE

According to another aspect of the disclosure, provided are methods directed to the use of the hair styling compositions described herein. The methods generally comprise applying any of the hair styling compositions described hair to hair. The hair styling compositions may be useful in a variety of settings, and either for chemically treated or untreated hair. Use on treated hair can include chemically relaxed/straightened hair or chemically dyed or bleached or lightened/highlighted hair. The application of the hair styling composition may be part of a pre-treatment, or after cleansing or conditioning or washing the hair as a leave-on treatment for styling/shaping the hair or caring for curly hair or as a leave-on or rinse-off mask treatment.

Methods of treating hair according to the disclosure may include applying a hair styling composition of the instant disclosure to the hair (wet, damp, or dry hair), allowing the hair treatment to remain on the hair for a sufficient amount of time, and rinsing the hair styling composition from the hair or allowing the hair treatment to be left on the hair as a leave-on product. The hair styling composition may be applied to the hair before, during, or after other hair styling compositions (e.g., a shampoo, a conditioner, a mask, a cream, a lotion, a gel, etc.). In some cases, the hair styling composition is used without other products.

Other methods of styling hair according to the disclosure involve a wash and go/braiding technique. Typically, the hair type on which this method is used is curly hair. Other methods of treating hair according to the disclosure involve a twist out technique. Typically, the hair type on which this method is used is curly hair.

The hair styling composition may be allowed to remain on the hair for a period of time, for example from about a few seconds (1, 3, 5, or 10 seconds) to about 10, 20, or 30 minutes, or longer. The hair styling compositions of the present disclosure can be used on hair of various curl types, the curl types ranging from slightly wavy to very kinky and coily hair.

Described above is the individual application of hair styling compositions or the combined or layered application of a hair styling composition with another composition. In some cases, a hair styling composition is individually applied to the hair and also combined or layered with another composition that is also applied to the hair.

Kits Containing Hair Styling Composition

The hair styling compositions of the instant disclosure may be incorporated into a kit. For example, the kits may include at least one hair styling composition according to the instant disclosure. The kits may also include one or more hair styling compositions (according the instant disclosure), a shampoo and/or a conditioner and/or a mask.

EMBODIMENTS

In certain embodiments, the hair styling compositions of the instant disclosure have a lamellar network and include:

- about 5 wt. % or more, preferably about 6 wt. % or more, more preferably 7 wt. % or more, of hydrogenated starch hydrolysate, such as sorbitol, maltitol, maltotriitol and other hydrogenated oligosaccharides and polysaccharides;
- about 3 wt. % or more, preferably about 4 wt. % or more, more preferably about 5 wt. % or more of polyol, including ethylene glycol, propylene glycol, butylene glycol, hexylene glycol, pentylene glycol, diethylene glycol, dipropylene glycol, 1,3 propanediol, glycerin, diglycerin, polyethylene glycols, or a mixture thereof; wherein a weight ratio of the total amount of hydrogenated starch hydrolysate to the total amount of polyol is from 1:1 to 10:1, preferably 1:1 to 5:1, or more preferably 1:1 to 2:1;
- about 1 to about 10 wt. %, preferably about 1 to about 8 wt. %, more preferably about 2 to about 7 wt. %, of a plant or vegetable based oil, wherein the plant or vegetable based oil comprises shea butter, castor oil, or a combination thereof;
- about 0.1 to about 7 wt. %, preferably about 0.2 to about 6 wt. %, preferably about 0.5 to about 4 wt. %, of a cationic surfactant, such as those chosen from cetrimonium chloride, steartrimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamidopropyidiethylamine, arachidamidoethyidiethylamine, arachidamidoethyidimethylamine, and a mixture thereof;
- about 0.5 to about 10 wt. %, preferably about 0.5 to about 8 wt. %, more preferably about 1 to about 8 wt. %, of emulsifiers, wherein the emulsifiers are chosen from:
  - a glyceryl ester, preferably at least one of glyceryl stearate and bis-diglyceryl polyacyladipate-2,
  - a fatty alcohol, such as those chosen from cetyl alcohol, stearyl alcohol, cetearyl alcohol, behenyl alcohol, lauryl alcohol (1-dodecanol); myristic or myristyl alcohol (1-tetradecanol), arachidyl alcohol (1-eicosanol), lignoceryl alcohol (1-tetracosanol); ceryl alcohol (1-hexacosanol); montanyl alcohol (1-octacosanol); myricylic alcohol (1-triacontanol), decyl alcohol, undecyl alcohol, and a mixture thereof, and
  - a mixture thereof; and
- water, preferably about 50 to about 90 wt. % of water, more preferably about 55 to about 85 wt. % of water, wherein all weight percentages are based on the total weight of the hair styling composition.

In further embodiments, the hair styling compositions of the instant disclosure have a lamellar network and include:

- about 5 wt. % or more, preferably about 6 wt. % or more, more preferably about 7 wt. % or more, of hydrogenated starch hydrolysate, such as sorbitol, maltitol, maltotriitol and other hydrogenated oligosaccharides and polysaccharides;
- about 3 wt. % or more, preferably about 4 wt. % or more, more preferably about 5 wt. % or more of polyol, including ethylene glycol, propylene glycol, butylene glycol, hexylene glycol, pentylene glycol, diethylene glycol, dipropylene glycol, 1,3 propanediol, glycerin, diglycerin, polyethylene glycols, or a mixture thereof; wherein a weight ratio of the total amount of hydrogenated starch hydrolysate to the total amount of polyol is from 1:1 to 5:1, preferably 1:1 to 4:1, or more preferably 1:1 to 2:1;
- about 1 to about 10 wt. %, preferably about 1 to about 8 wt. %, more preferably about 2 to about 7 wt. %, of a plant or vegetable based oil, wherein the plant or vegetable based oil comprises shea butter, castor oil, or a combination thereof;
- about 0.1 to about 7 wt. %, preferably about 0.2 to about 6 wt. %, preferably about 0.5 to about 4 wt. %, of a cationic surfactant, wherein the cationic surfactant is preferably behentrimonium chloride;
- about 0.5 to about 10 wt. %, preferably about 0.5 to about 8 wt. %, more preferably about 1 to about 8 wt. %, of emulsifiers, wherein the emulsifiers are chosen from:
  - about 0.1 to about 9.8 wt. % of a glyceryl ester, preferably at least one of glyceryl stearate and bis-diglyceryl polyacyladipate-2,
  - about 0.1 to about 9.8 wt. % of a fatty alcohol, such as those chosen from cetyl alcohol, stearyl alcohol, cetearyl alcohol, behenyl alcohol, lauryl alcohol (1-dodecanol); myristic or myristyl alcohol (1-tetradecanol), arachidyl alcohol (1-eicosanol), lignoceryl alcohol (1-tetracosanol); ceryl alcohol (1-hexacosanol); montanyl alcohol (1-octacosanol); myricylic alcohol (1-triacontanol), decyl alcohol, undecyl alcohol, and a mixture thereof, and
  - a mixture thereof; and
- about 50 wt. % or more water, preferably about 50 to about 90 wt. % of water, more preferably about 55 to about 85 wt. % of water; and about 0.1 to about 10 wt. %, preferably about 0.1 wt. % to about 8 wt. %, more preferably about 0.2 wt. % to about 6 wt. %, of a thickening agent including those chosen from hydroxypropyl guar, xanthan gum, guar gum, biosaccharide gum, cellulose, acacia seneca gum, sclerotium gum, agarose, pechtin, gellan gum, ammonium polyacryloyldimethyl taurate, ammonium acryloyldimethyltaurate/VP copolymer, sodium polyacrylate, acrylates copolymers, polyacrylamide, carbomer, acrylates/C10-30 alkyl acrylate crosspolymer, acrylates/beheneth-25 methacrylate copolymer, and a mixture thereof, wherein all weight percentages are based on the total weight of the hair styling composition.

In further embodiments, a method for treating hair includes:

(I) applying a hair styling composition to hair, the hair styling composition comprising:

about 5 wt. % or more, preferably about 6 wt. % or more, preferably about 7 wt. % or more, of hydrogenated starch hydrolysate, such as sorbitol, maltitol, maltotriitol and other hydrogenated oligosaccharides and polysaccharides;

about 3 wt. % or more, preferably about 4 wt. % or more, more preferably about 5 wt. % or more of polyol, including ethylene glycol, propylene glycol, butylene glycol, hexylene glycol, pentylene glycol, diethylene glycol, dipropylene glycol, 1,3 propanediol, glycerin, diglycerin, polyethylene glycols, or a mixture thereof;

wherein a weight ratio of the total amount of hydrogenated starch hydrolysate to the total amount of polyol is from 1:1 to 10:1, preferably 1:1 to 5:1, or more preferably 1:1 to 2:1;

about 1 to about 10 wt. %, preferably about 1 to about 8 wt. %, more preferably about 2 to about 7 wt. %, of a plant or vegetable based oil, wherein the plant or vegetable based oil comprises shea butter, castor oil, or a combination thereof;

about 0.1 to about 7 wt. %, preferably about 0.2 to about 6 wt. %, preferably about 0.5 to about 4 wt. %, of a cationic surfactant, such as those chosen from cetrimonium chloride, steartrimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethylamine, behenamidoethyldimethylamine, arachidamidopropyldimethylamine, arachidamido-propyidiethylamine, arachidamidoethyidiethylamine, arachidamidoethyidimethylamine, and a mixture thereof;

about 0.5 to about 10 wt. %, preferably about 0.5 to about 8 wt. %, more preferably about 1 to about 8 wt. %, of emulsifiers, wherein the emulsifiers are chosen from:

a glyceryl ester, preferably at least one of glyceryl stearate and bis-diglyceryl polyacyladipate-2, and a fatty alcohol, such as those chosen from cetyl alcohol, stearyl alcohol, cetearyl alcohol, behenyl alcohol, lauryl alcohol (1-dodecanol); myristic or myristyl alcohol (1-tetradecanol), arachidyl alcohol (1-eicosanol), lignoceryl alcohol (1-tetracosanol); ceryl alcohol (1-hexacosanol); montanyl alcohol (1-octacosanol); myricylic alcohol (1-triacontanol), decyl alcohol, undecyl alcohol, and a mixture thereof, and a mixture thereof; and water, preferably about 50 to about 90 wt. % of water, more preferably about 55 to about 85 wt. % of water, wherein all weight percentages are based on the total weight of the hair styling composition.

(II) styling the hair, wherein the hair is styled within 20 minutes of application of the hair styling composition to the hair.

Examples

The following non-limiting examples are provided primarily for the purposes of elucidating the benefits and properties achieved by aspects of the invention.

Example 1

| | | | INCI (U.S.) Name | Ex. A (Wt. %) | Ex. B (Wt. %) | Comp. 1 (Wt. %) |
|---|---|---|---|---|---|---|
| (a) | Hydrogenated starch hydrolysate | | HYDROGENATED STARCH HYDROLYSATE | 7 | 7 | |
| (b) | Polyols | | GLYCERIN, DIPROPYLENE GLYCOL, and/or CAPRYLYL GLYCOL | 5.3 | 5.9 | 2.5 |
| | Weight ratio of hydrogenated starch hydrolysate of (a) to polyols of (b) | | | 1.3:1 | 1.2:1 | |
| (c) | Plant or Vegetable based Oils | | RICINUS COMMUNIS (CASTOR) SEED OIL | 2 | 2 | |
| | | | BUTYROSPERMUM PARKII (SHEA) BUTTER | 2 | 2 | 0.5 |
| | | | COCOS NUCIFERA (COCONUT) OIL | | | 0.5 |
| (d) | Cationic Surfactant | | BEHENTRIMONIUM CHLORIDE | 1.58 | 1.4 | |
| (e) | Emulsifiers | Glyceryl Ester | GLYCERYL STEARATE | 1 | 1 | |
| | | | BIS-DIGLYCERYL POLYACYLADIPATE-2 | 1 | 3 | 1 |
| | | Glucoside | CETEARYL GLUCOSIDE | | | 0.6 |
| | | Fatty Alcohol | CETEARYL ALCOHOL | 3 | 3 | 2.4 |
| | | Fatty | CETYL ESTERS | 0.25 | 0.25 | |

-continued

| | | INCI (U.S.) Name | Ex. A (Wt. %) | Ex. B (Wt. %) | Comp. 1 (Wt. %) |
|---|---|---|---|---|---|
| | Ester(s) | ISOPROPYL MYRISTATE | | | 2 |
| (g) | Thickening Agent | HYDROXYPROPYL GUAR | 1.25 | 1.25 | 1.25 |
| | | SCLEROTIUM GUM | | | 0.25 |
| | Misc. | CITRIC ACID, PHENOXYETHANOL, ISOPROPYL ALCOHOL, and/or SODIUM BENZOATE | 1.06 | 0.7 | 0.6 |
| | Fragrance | FRAGRANCE | 0.9 | 0.9 | 0.9 |
| (f) | Water | WATER | QS to 100 | QS to 100 | QS to 100 |

Example 2

Figure 3:
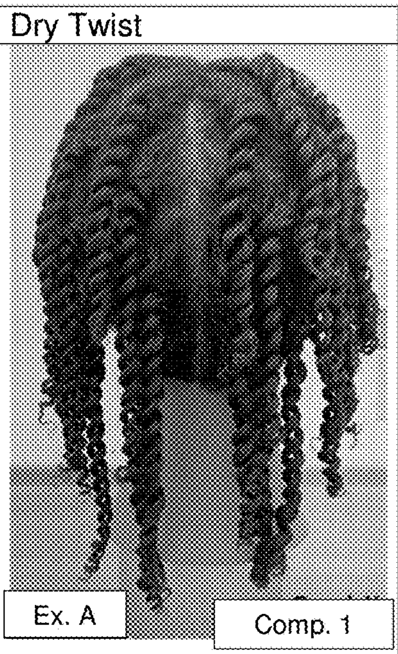
FIG. 3 provides images of mannequin hair styled with a comparative hair styling composition and an exemplary hair styling composition in accordance with aspects of the disclosure.
Figure 3:
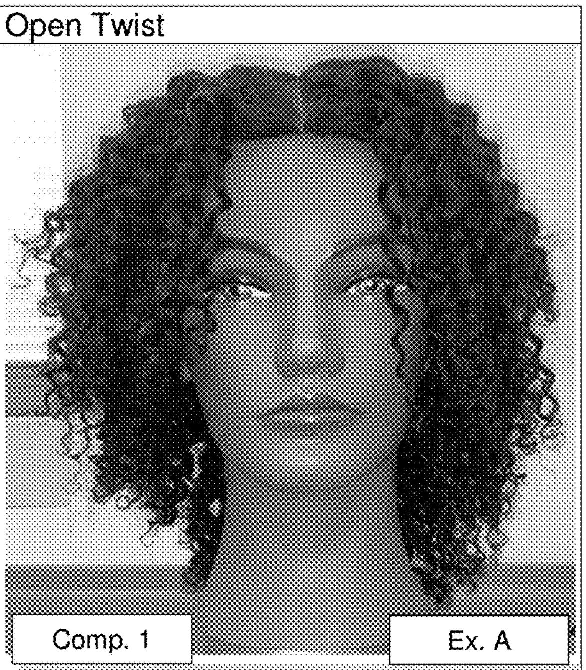
Figure 3:
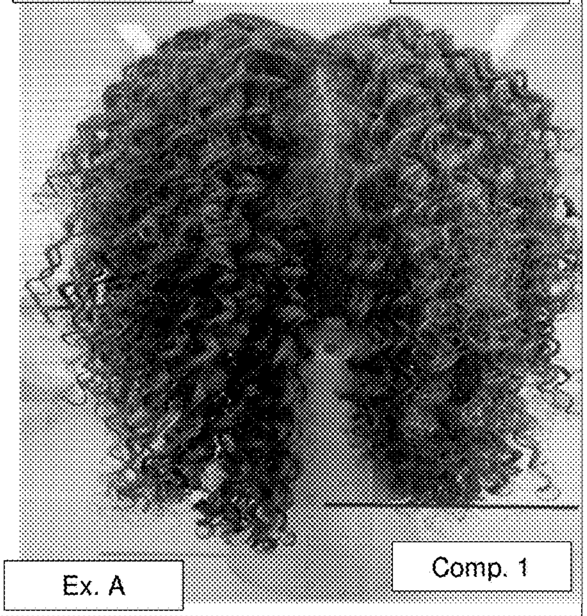

Example Composition A and Comparative Composition 1 were applied to a mannequin and assessed on various visual properties. The hair of the mannequin was then stylized with a dry twist or open twist. As shown in FIG. 3, Example Composition A provided better elongation of the hair while also providing better visual properties than Comparative Composition 1. For example, as seen with the dry twist style, Example Composition A exhibited tighter curls, better holding twist, no visual residue, and more visual length then Comparative Composition 1. Similarly, Example Composition A exhibited no visual residue (which was a significant improvement over Comparative Composition A), softer conditioned feel, and more visual length then Comparative Composition 1 for the open twist style.

Example 3

Example Composition A was assessed in comparison to a commercial benchmark (Comparative Composition 2) to determine the resiliency and elasticity of the both compositions on hair. Comparative Composition 2 has the following list of ingredients (based on the product label).

Ingredients: Water, Cetearyl Alcohol, *Linum usitatissimum* (Linseed) Seed Oil, *Butyrospermum parkii* (Shea) Butter*~, Glycerin (Vegetable), Stearyl Alcohol, Behentrimonium Methosulfate, Cetyl Alcohol, *Prunus amygdalus dulcis* (Sweet Almond) Oil, Behentrimonium Chloride, Fragrance (Essential Oil Blend), Panthenol, *Elaeis guineensis* (Palm) Oil, Hydrolyzed Soy Protein, *Theobroma cacao* (Cocoa) Seed Butter, *Persea gratissima* (Avocado) Oil, Hydrogenated Vegetable Oil, Tocopherol, Cetrimonium Chloride, *Glycyrrhiza glabra* (Licorice) Root Extract, *Camellia sinensis* (Green Tea) Leaf Extract, *Equisetum arvense* Extract, Triethyl Citrate, Caprylyl Glycol, Benzoic Acid.

Example Composition A and Comparative Composition 2 were evaluated to determine the storage modulus over a range of oscillation stress after samples of Example Composition A and Comparative Composition 2 had dried for a specified amount of time. 10 g of each sample was weighed in a polystyrene weighing boat (3.5 in×3.5 in×1 in) and dried at RT (room temperature) or 60° C. for certain period of time. A DHR-3 rheometer, commercially available from TA INSTRUMENTS, with a 40 mm parallel plate, was employed to evaluate the rheological properties of each sample. Dynamic strain sweep measurements were carried out to determine the storage modulus in linear viscoelastic regime and yield stress with a strain range from 0.001 to 100%. The yield stress was taken as the onset value of the storage modulus curve.

The storage modulus for Example Composition A and Comparative Composition 2 was evaluated after drying overnight at room temperature, after drying overnight at 60° C., after drying at room temperature for 3 days, after drying at room temperature for 6 days, and after drying at room temperature for 10 days. The results of the storage modulus and yield stress evaluation of Example Composition A and Comparative Composition B are provided in the table below.

| | Storage Modulus (Pa) | | Yield Stress (Pa) | |
|---|---|---|---|---|
| | Ex. A | Comp. 2 | Ex. A | Comp. 2 |
| Formula itself | 930 | 2900 | 61.5 | 106.3 |
| overnight dry at RT | 1720 | 4780 | 61.9 | 102.5 |
| 3 days dry at RT | 3860 | 5900 | 180.6 | 142.8 |
| 6 days dry at RT | 9733 | 9900 | 289 | 253.8 |
| 10 days dry at RT | 24350 | 26030 | 960.1 | 103.3 |
| overnight dry at 60° C. | 19230 | 41633 | 630.5 | 148.1 |

Figure 4:
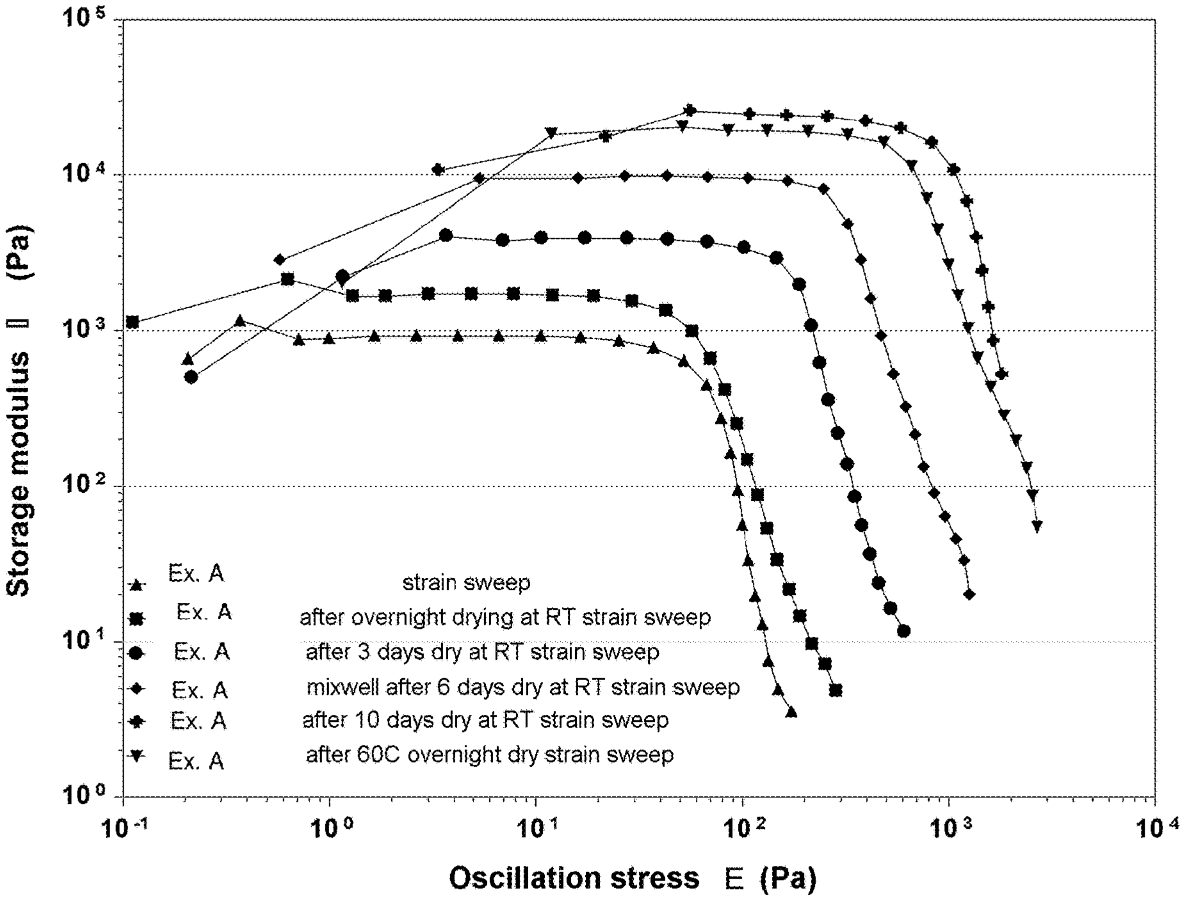
FIG. 4 is a graph of the storage modulus for Example Composition A after different amounts of drying according to aspects of the disclosure.

As shown in FIG. 4, there was an increase in the storage modulus of Example Composition A associated with an increase in the amount of drying time. Moreover, the yield stress, which is the amount of oscillation stress before there is a significant decrease in storage modulus, also increased with the amount of drying time for Example Composition A that were dried for longer amounts of time. Accordingly, Example Composition A exhibited a significant increase both in storage modulus and yield stress, which is indicative of an increase in durability (elastic and strong) and increase in resiliency as Example Composition A dried.

Figure 5:
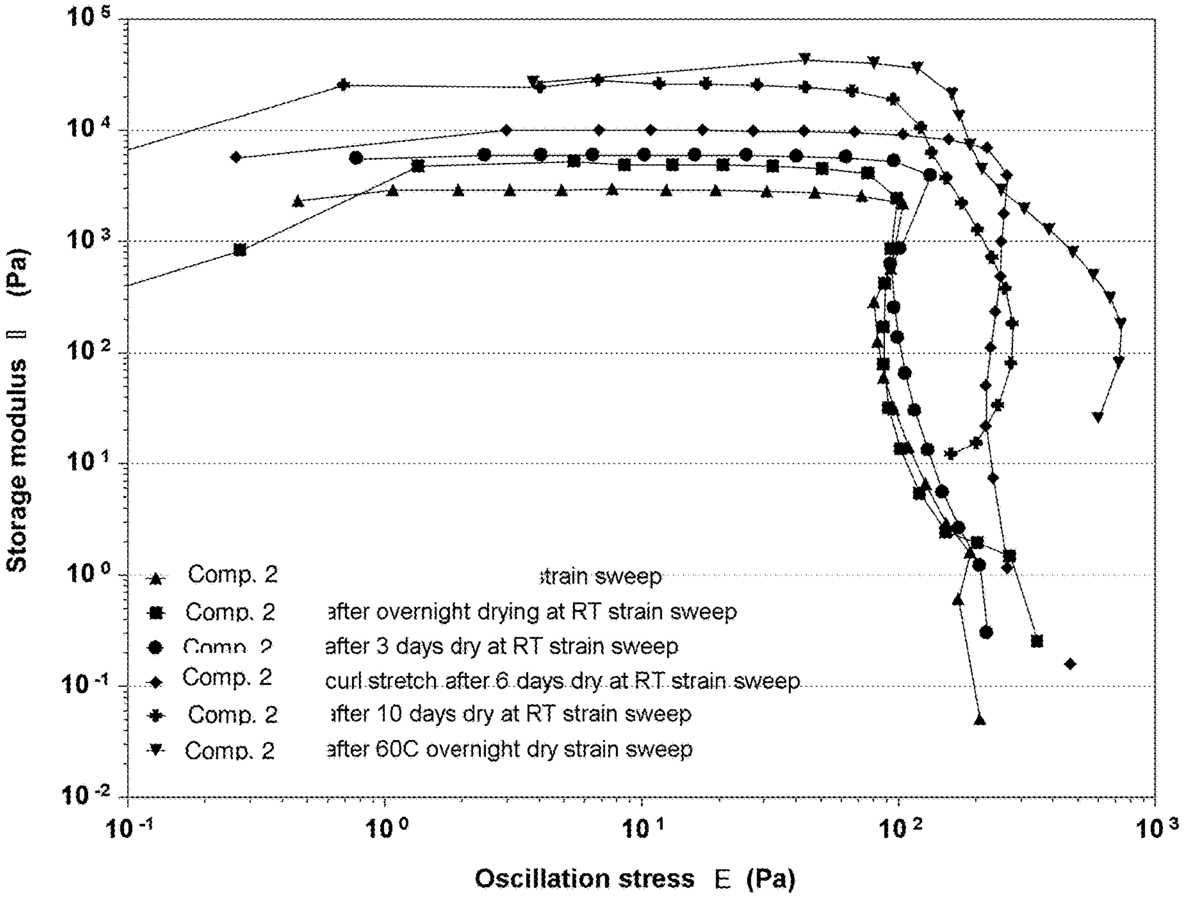
FIG. 5 is a graph of the storage modulus for Comparative Composition 2 after different amounts of drying.

As shown in FIG. 5, Comparative Composition 2 exhibited an increase in the storage modulus for samples that were dried for longer amounts of time. However, Comparative Composition 2 did not exhibit a significant nor a consistent increase in the yield stress. This indicates that Comparative Composition 2 became more brittle as it underwent longer amounts of drying time.

Accordingly, Example Composition A provided improved durability and resiliencies, especially in comparison to Comparative Composition 2, a commercial benchmark.

Example 4

Example Composition A was evaluated in comparison to Comparative Example 3. Comparative Example 3 had the same formulation as Example Composition A except that it did not include bis-diglyceryl polyacyladipate-2. Samples of Example Composition A and Comparative Example 3 were applied to eight human volunteers, each having short curly hair that was identified as curl pattern 8.

During the wet application, Example Composition A exhibited a faster application, more grip, and easier detangling of the hair. Comparative Composition 3 was more slippery and the hair was difficult to detangle in comparison to Example Composition A.

Example Composition A and Comparative Composition 3 were allowed to dry on the volunteer's hair and then evaluated. Example Composition A exhibited more topical, more movement, and more pliability properties to the hair than Comparative Composition 3. Comparative Composition 3 exhibited more volume, slightly more stiffness, and more frizz than Example Composition A.

It was unexpected that bis-diglyceryl polyacyladipate-2 in combination with all the of other ingredients of Example Composition A would provide improvements to the various attributes of hair.

The term "INCI" is an abbreviation of International Nomenclature of Cosmetic Ingredients, which is a system of names provided by the International Nomenclature Committee of the Personal Care Products Council to describe personal care ingredients.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc.

All components and elements positively set forth in this disclosure can be negatively excluded from the claims. In other words, the hair styling compositions of the instant disclosure can be free or essentially free of all components and elements positively recited throughout the instant disclosure.

In some instances, the hair styling compositions of the present disclosure may be substantially free of non-incidental amounts of the ingredient(s) or compound(s) described herein. A non-incidental amount of an ingredient or compound is the amount of that ingredient or compound that is added into the hair styling composition by itself. For example, a hair styling composition may be substantially free of a non-incidental amount of an ingredient or compound, although such ingredient(s) or compound(s) may be present as part of a raw material that is included as a blend of two or more compounds.

Some of the various categories of components identified may overlap. In such cases where overlap may exist and the composition includes both components (or the composition includes more than two components that overlap), an overlapping compound does not represent more than one component. For example, steareth-20 may be characterized as both an alkoxylated fatty alcohols and a nonionic surfactant. If a particular composition includes both an alkoxylated fatty alcohols and a nonionic surfactant, steareth-20 will serve only as the alkoxylated fatty alcohols or only as the alkoxylated fatty alcohols (steareth-20 does not serve as both the alkoxylated fatty alcohols and nonionic surfactant).

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

As used herein, the terms "comprising," "having," and "including" are used in their open, non-limiting sense.

The terms "a," "an," and "the" are understood to encompass the plural as well as the singular. Thus, the term "a mixture thereof" also relates to "mixtures thereof." Throughout the disclosure, the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

The expression "one or more" means "at least one" and thus includes individual components as well as mixtures/combinations.

Other than in the operating examples, or where otherwise indicated, all numbers expressing quantities of ingredients and/or reaction conditions may be modified in all instances by the term "about," meaning within +/−5% of the indicated number.

The term "treat" (and its grammatical variations) as used herein refers to the application of the compositions of the present disclosure onto the surface of keratinous substrates such as hair on a user's head and/or body.

The term "substantially free" or "essentially free" as used herein means that there is less than about 2% by weight of a specific material added to a composition, based on the total weight of the compositions. Nonetheless, the compositions may include less than about 1 wt. %, less than about 0.5 wt. %, less than about 0.1 wt. %, or none of the specified material. All of the components set forth herein may be optionally included or excluded from the compositions/method/kits. When excluded, the compositions/methods/kits may be free or essentially free of the component. For example, a particular composition may be free or essentially free of silicones.

What is claimed is:

1. A hair styling composition comprising:

(a) about 5 wt. % or more of hydrogenated starch hydrolysate;

(b) about 3 wt. % or more of polyol, wherein a weight ratio of the total amount of hydrogenated starch hydrolysate to the total amount of polyol is from 1:1 to 10:1;

(c) about 1 to about 10 wt. % of a plant or vegetable based oil, wherein the plant or vegetable based oil comprise shea butter, castor oil, or a combination thereof;

(d) about 0.1 to about 7 wt. % of a cationic surfactant;

(e) about 0.5 to about 10 wt. % of emulsifiers, wherein the emulsifiers are chosen from:

a glyceryl ester, a fatty alcohol having more than 8 carbon atoms, and a mixture thereof; and (f) water, wherein all weight percentages are based on the total weight of the hair styling composition; and wherein the hair styling composition is in the form of a lamellar network.

2. The hair styling composition of claim 1, wherein the weight ratio of the total amount of hydrogenated starch hydrolysate to the total amount of polyol is 1:1 to 5:1.

3. The hair styling composition of claim 2, wherein the weight ratio of the total amount of hydrogenated starch hydrolysate to the total amount of polyol is 1:1 to 2:1.

4. The hair styling composition of claim 1, comprising about 5 wt. % to about 15 wt. % of polyol.

5. The hair styling composition of claim 4, wherein the polyol is chosen from ethylene glycol, propylene glycol, butylene glycol, hexylene glycol, pentylene glycol, diethylene glycol, dipropylene glycol, 1,3 propanediol, glycerin, diglycerin, polyethylene glycols, and a mixture thereof.

6. The hair styling composition of claim 1, wherein the plant or vegetable based oil comprises castor oil and shea butter.

7. The hair styling composition of claim 1, wherein the plant or vegetable based oil further comprises coconut oil, soybean oil, canola oil, rapeseed oil, corn oil, cottonseed oil, olive oil, palm oil, peanut oil, safflower oil, sesame oil, sunflower oil, linseed oil, palm kernel oil, tung oil, jatropha oil, mustard oil, camelina oil, pennycress oil, castor oil, wheat germ oil, apricot kernel oil, pistachio oil, poppy oil, pine oil, avocado oil, hazel nut oil, grapeseed oil, colza oil, cade oil, peach kernel oil, coffee bean oil, jojoba oil, or a mixture thereof.

8. The hair styling composition of claim 1, wherein the cationic surfactant is chosen from wherein the cationic surfactant is chosen from cetrimonium chloride, steartrimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, and a mixture thereof.

9. The hair styling composition of claim 1, wherein the fatty alcohol is chosen from cetyl alcohol, stearyl alcohol, cetearyl alcohol, behenyl alcohol, lauryl alcohol (1-dodecanol); myristic or myristyl alcohol (1-tetradecanol), arachidyl alcohol (1-eicosanol), lignoceryl alcohol (1-tetracosanol); ceryl alcohol (1-hexacosanol); montanyl alcohol (1-octacosanol); myricylic alcohol (1-triacontanol), decyl alcohol, undecyl alcohol, and a mixture thereof.

10. The hair styling composition of claim 1, wherein the emulsifier further comprises:

about 0.1 to about 15 wt. % of a fatty ester that is not glyceryl ester, wherein the fatty ester that is not glyceryl ester is chosen from isopropyl esters, cetyl esters, isopropyl myristate, isopropyl laurate, isopropyl oleate, isopropyl palmitate, isopropyl stearate, and a mixture thereof.

11. The hair styling composition of claim 1 further comprising:

(g) about 0.01 to about 10 wt. % of a thickening agent chosen from hydroxypropyl guar, xanthan gum, guar gum, biosaccharide gum, cellulose, acacia seneca gum, sclerotium gum, agarose, pechtin, gellan gum, ammonium polyacryloyldimethyl taurate, ammonium acryloyldimethyltaurate/VP copolymer, sodium polyacrylate, acrylates copolymers, polyacrylamide, carbomer, acrylates/C10-30 alkyl acrylate crosspolymer, acrylates/beheneth-25 methacrylate copolymer, and a mixture thereof.

12. The hair styling composition of claim 1, wherein the storage modulus of the hair styling composition increases with an amount drying time.

13. The hair styling composition of claim 1, wherein the yield stress of the hair styling composition increases with an amount of drying time.

14. A hair styling composition comprising:

(a) about 5 wt. % or more of hydrogenated starch hydrolysate;

(b) about 3 wt. % or more of polyol, wherein a weight ratio of the total amount of hydrogenated starch hydrolysate to the total amount of polyol is from 1:1 to 5:1;

(c) about 1 to about 10 wt. % of a plant or vegetable based oil, wherein the plant or vegetable based oil comprise shea butter, castor oil, or a combination thereof;

(d) about 0.1 to about 7 wt. % of a cationic surfactant;

(e) about 0.5 to about 10 wt. % of emulsifiers, wherein the emulsifiers are chosen from:

about 0.1 to about 9.8 wt. % of a glyceryl ester about 0.1 to about 9.8 wt. % of a fatty alcohol having more than 8 carbon atoms, and a mixture thereof;

(f) about 50 wt. % or more of water; and (g) about 0.1 to about 10 wt. % of a thickening agent, wherein all weight percentages are based on the total weight of the hair styling composition; and wherein the hair styling composition is in the form of a lamellar network.

15. The hair styling composition of claim 14, wherein the weight ratio of the total amount of hydrogenated starch hydrolysate to the total amount of polyol is 1:1 to 2:1.

16. The hair styling composition of claim 14, wherein the polyol is glycerin.

17. The hair styling composition of claim 14, wherein the cationic surfactant is behentrimonium chloride.

18. The hair styling composition of claim 14, wherein the glyceryl ester is chosen from glyceryl stearate, bis-diglyceryl polyacyladipate-2, glyceryl behenate, glyceryl caprate, glyceryl cocoate, glyceryl erucate, glyceryl hydroxystearate, glyceryl isostearate, glyceryl lanolate, glyceryl laurate, glyceryl linoleate, glyceryl myristate, glyceryl oleate, glyceryl palmitate lactate, glyceryl sesquioleate,, glyceryl stearate citrate, glyceryl stearate lactate, glyceryl dioleate, glyceryl distearate, glyceryl laurate, or a mixture thereof.

19. A method for hair styling comprising:

(I) applying a hair styling composition to hair, the hair styling composition comprising:

(a) about 5 wt. % or more of hydrogenated starch hydrolysate;

(b) about 3 wt. % or more of polyol, wherein a weight ratio of the total amount of hydrogenated starch hydrolysate to the total amount of polyol is from 1:1 to 10:1;

(c) about 1 to about 10 wt. % of a plant or vegetable based oil, wherein the plant or vegetable based oil comprise shea butter, castor oil, or a combination thereof;

(d) about 0.1 to about 7 wt. % of a cationic surfactant;

(e) about 0.5 to about 10 wt. % of emulsifiers, wherein the emulsifiers are chosen from:

a glyceryl ester, a fatty alcohol having more than 8 carbon atoms, and a mixture thereof; and (f) water, wherein all weight percentages are based on the total weight of the hair styling composition; and wherein the hair styling composition is in the form of a lamellar network; and (II) styling the hair.

20. The method for hair styling of claim 19, wherein the hair is styled within 20 minutes of application of the hair styling composition to the hair.

21. The hair styling composition of claim 1, which is a rinse-off composition.

22. The hair styling composition of claim 1, wherein the emulsifier comprises glyceryl stearate and bis-diglyceryl polyacyladipate-2.

23. The hair styling composition of claim 1, wherein the emulsifier comprises a fatty alcohol from cetyl alcohol, stearyl alcohol, cetearyl alcohol, behenyl alcohol, lauryl alcohol (1-dodecanol); myristic or myristyl alcohol (1-tetradecanol), arachidyl alcohol (1-eicosanol), lignoceryl alcohol (1-tetracosanol); ceryl alcohol (1-hexacosanol); montanyl alcohol (1-octacosanol); myricylic alcohol (1-triacontanol), decyl alcohol, undecyl alcohol, and a mixture thereof.

24. The hair styling composition of claim 1, wherein the fatty alcohol comprises cetearyl alcohol.

25. The hair styling composition of claim 14, which comprises (a) about 5 to about 20 wt. % of the hydrogenated starch hydrolysate; (b) about 5 wt. % to about 15 wt. % of the polyol; wherein the fatty alcohol is selected from the group consisting of cetyl alcohol, stearyl alcohol, cetearyl alcohol, behenyl alcohol, lauryl alcohol (1-dodecanol); myristic or myristyl alcohol (1-tetradecanol), arachidyl alcohol (1-eicosanol), lignoceryl alcohol (1-tetracosanol); ceryl alcohol (1-hexacosanol); montanyl alcohol (1-octacosanol); myricylic alcohol (1-triacontanol), decyl alcohol, undecyl alcohol, and a mixture thereof; and (f) about 50 to about 85 wt. % of water.

26. The hair styling composition of claim 25, wherein the emulsifier comprises glyceryl stearate and bis-diglyceryl polyacyladipate-2.

* * * * *